United States Patent
Yoshioka et al.

(10) Patent No.: US 12,133,626 B2
(45) Date of Patent: Nov. 5, 2024

(54) ENDOSCOPE SYSTEM AND ENDOSCOPE SYSTEM OPERATION METHOD

(71) Applicant: FUJIFILM Corporation, Tokyo (JP)

(72) Inventors: Masato Yoshioka, Kanagawa (JP); Takeshi Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 41 days.

(21) Appl. No.: 18/160,173

(22) Filed: Jan. 26, 2023

(65) Prior Publication Data

US 2023/0240511 A1 Aug. 3, 2023

(30) Foreign Application Priority Data

Feb. 1, 2022 (JP) .................................. 2022-014070

(51) Int. Cl.
*A61B 1/00* (2006.01)
*A61B 1/06* (2006.01)

(52) U.S. Cl.
CPC ............ *A61B 1/00009* (2013.01); *A61B 1/06* (2013.01)

(58) Field of Classification Search
CPC . A61B 1/00009; A61B 1/06; A61B 1/000096; A61B 1/000094; A61B 1/0005; A61B 1/00096; A61B 1/0623; A61B 1/063; A61B 1/0676; A61B 5/1076
See application file for complete search history.

(56) References Cited

U.S. PATENT DOCUMENTS

| | | |
|---|---|---|
| 2019/0204069 A1 | 7/2019 | Tatsuta et al. |
| 2020/0008661 A1* | 1/2020 | Yoshioka ............ G02B 23/2461 |
| 2022/0007921 A1 | 1/2022 | Yoshioka et al. |
| 2022/0330850 A1* | 10/2022 | Yoshioka ................. G06T 7/60 |

FOREIGN PATENT DOCUMENTS

| | | |
|---|---|---|
| EP | 4 024 113 A1 | 7/2022 |
| EP | 4 083 677 A1 | 11/2022 |
| WO | 2018/051680 A1 | 3/2018 |
| WO | 2021/039718 A1 | 3/2021 |
| WO | WO-2021131238 A1 * | 7/2021 ....... A61B 1/000094 |

OTHER PUBLICATIONS

Communication Pursuant to Article 94(3) EPC issued by the European Patent Office on Feb. 29, 2024, which corresponds to EP 23 154 377.8-1113 and is related to U.S. Appl. No. 18/160,173.

The extended European search report issued by the European Patent Office on Jun. 23, 2023, which corresponds to European Patent Application No. 23154377.8-1113 and is related to U.S. Appl. No. 18/160,173.

* cited by examiner

*Primary Examiner* — Mohammed S Rahaman
(74) *Attorney, Agent, or Firm* — Studebaker & Brackett PC

(57) ABSTRACT

A captured image including a specific region formed by auxiliary measurement light is acquired, a marker direction candidate position is detected on the basis of region-of-interest edge information extracted from the captured image and specified distance position information, a candidate distance from the position of the specific region to the marker direction candidate position is calculated, and a length measurement image in which a display marker, which passes through a part of an extension line passing through the marker direction candidate position, which forms a candidate distance equal to or larger than a specified distance from the position of the specific region, is superimposed on the captured image with the position of the specific region as a base point, is created and displayed.

15 Claims, 22 Drawing Sheets

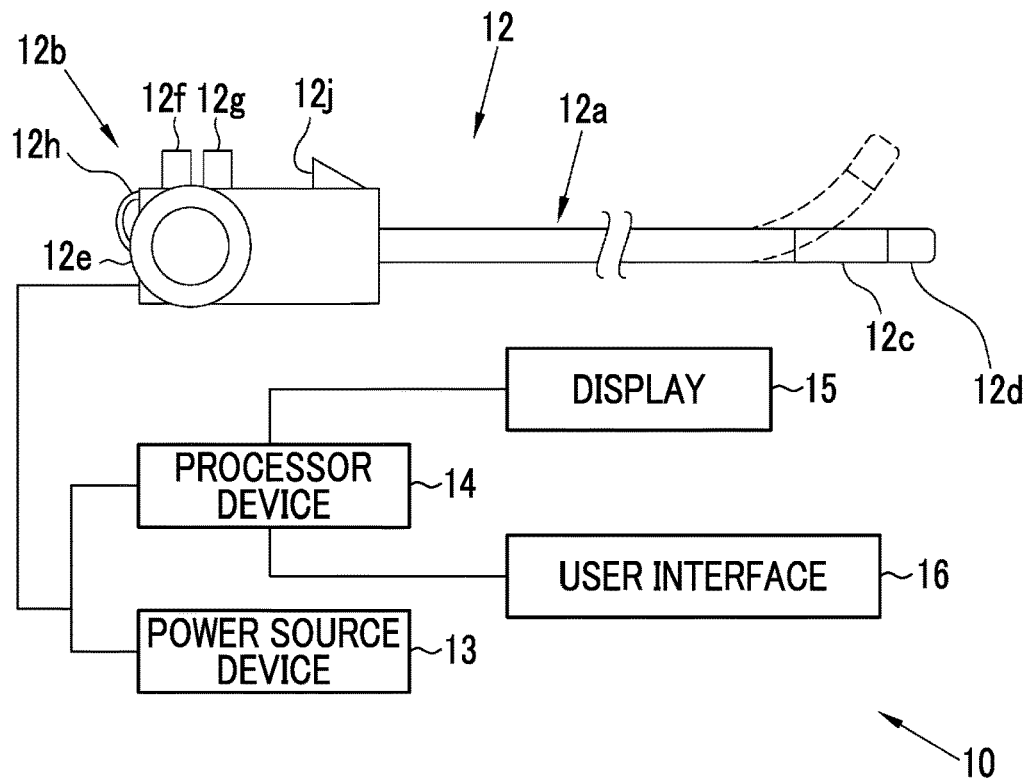
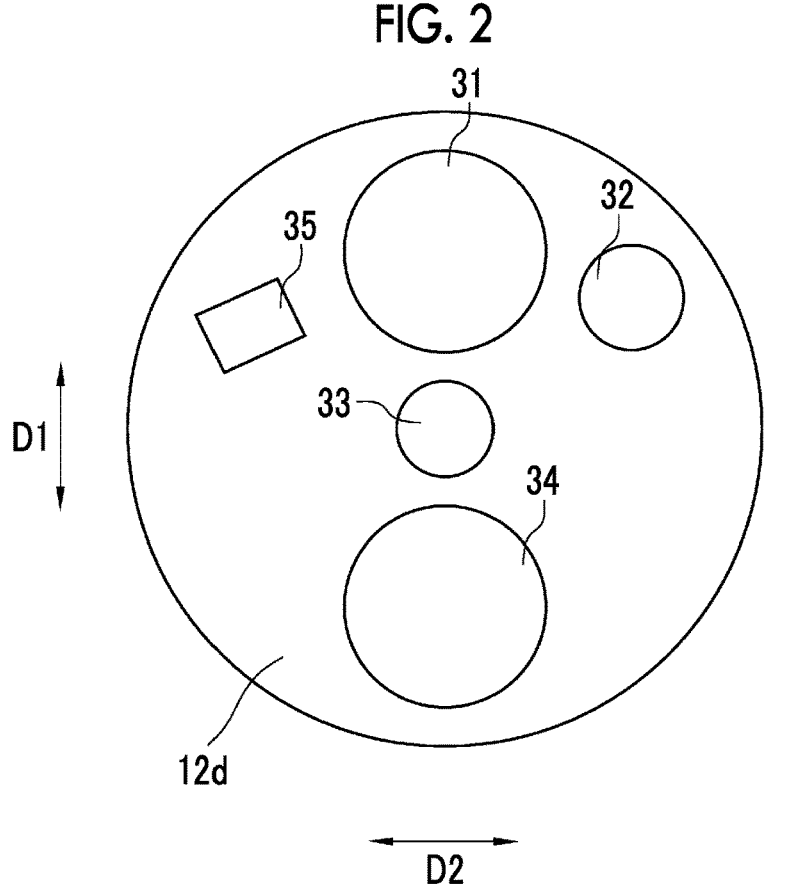

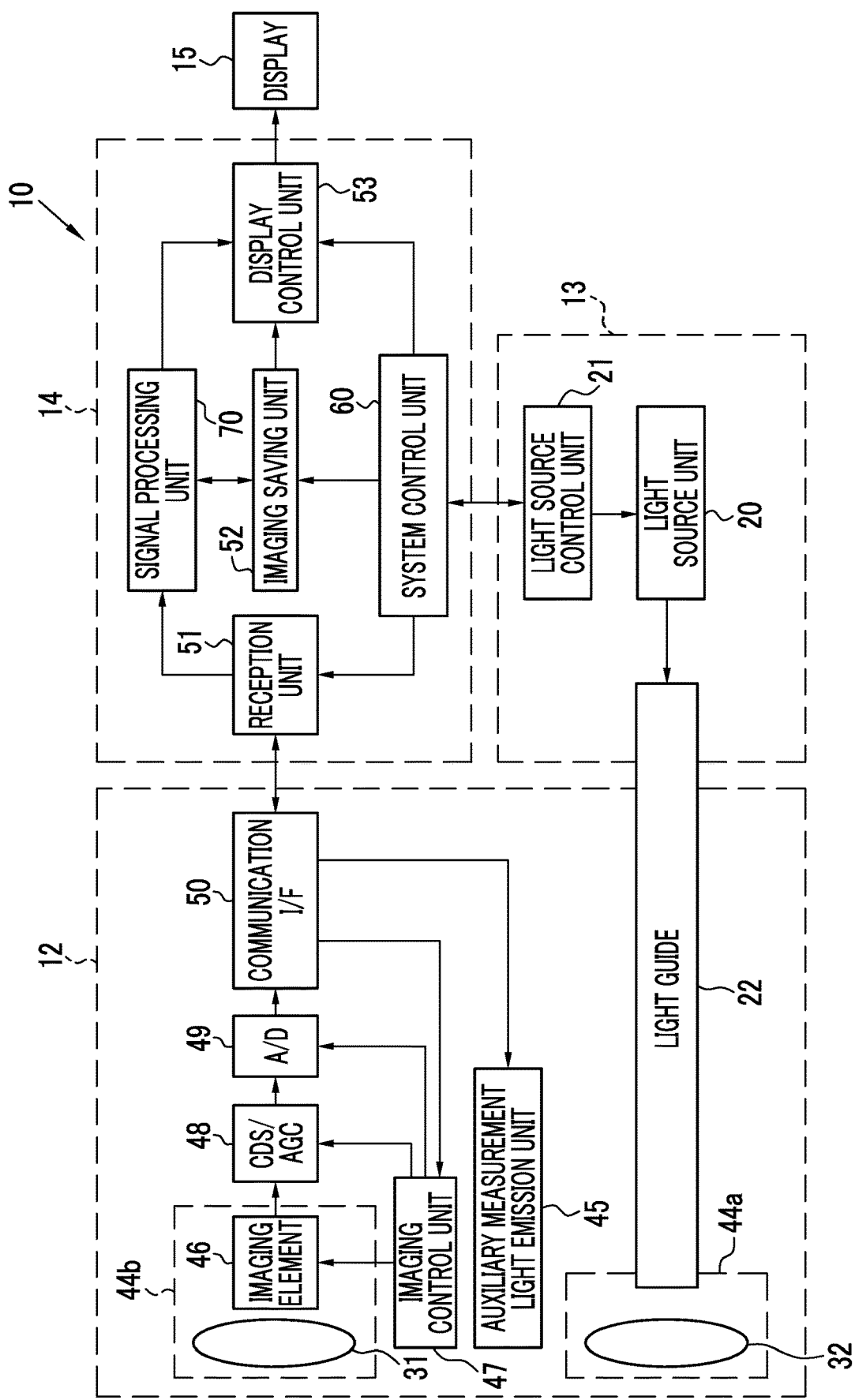

FIG. 32
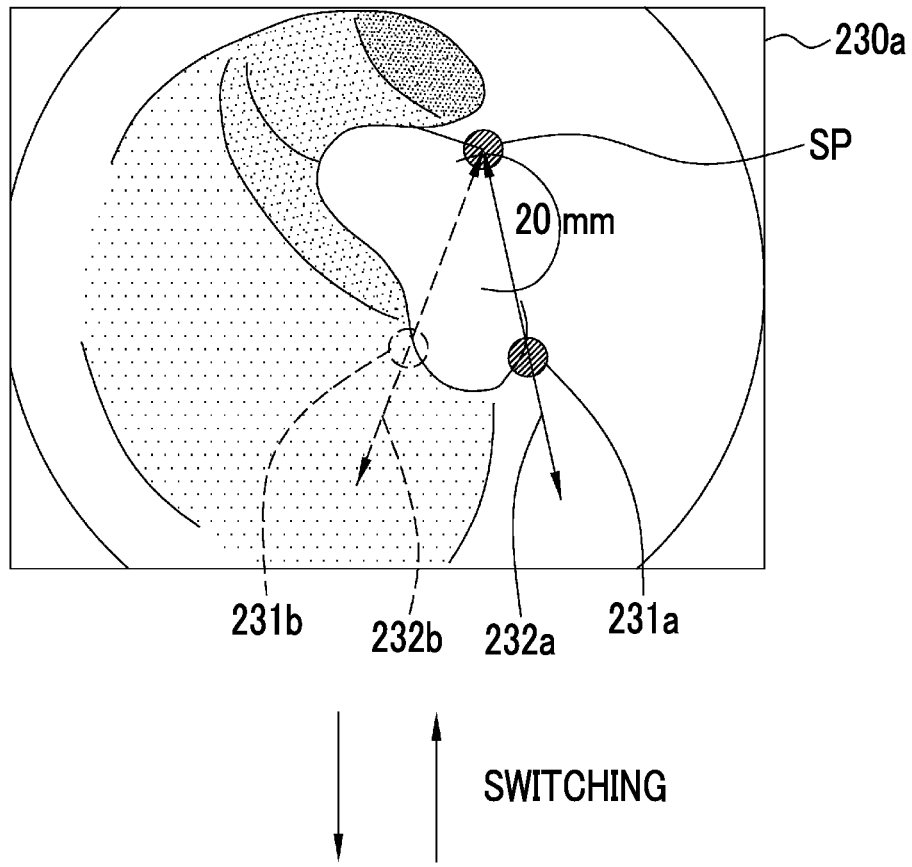
SWITCHING
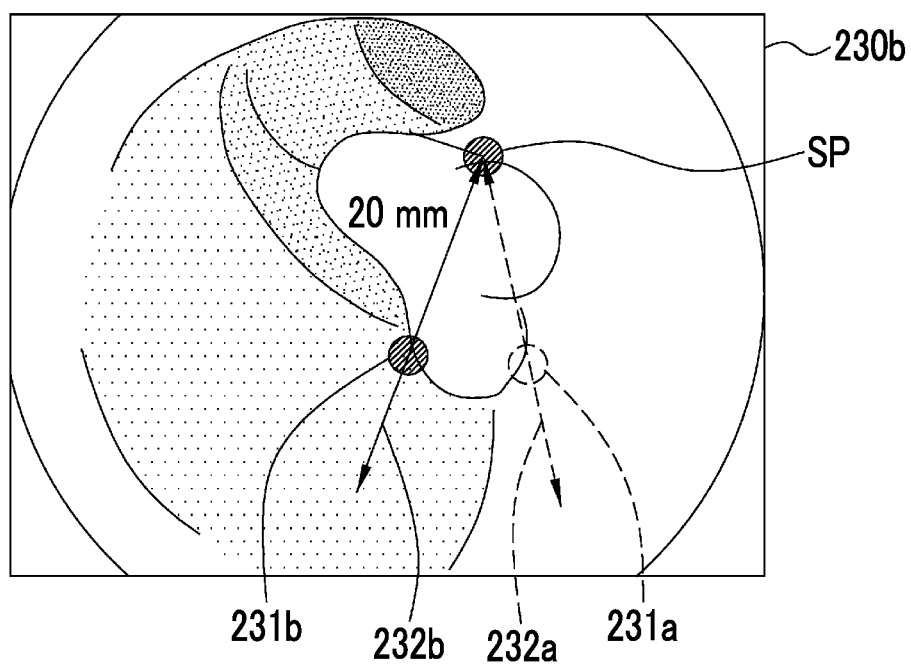

ENDOSCOPE SYSTEM AND ENDOSCOPE SYSTEM OPERATION METHOD

CROSS-REFERENCE TO RELATED APPLICATIONS

This application claims priority under 35 U.S.C § 119(a) to Japanese Patent Application No. 2022-014070 filed on 1 Feb. 2022. The above application is hereby expressly incorporated by reference, in its entirety, into the present application.

BACKGROUND OF THE INVENTION

1. Field of the Invention

The present invention relates to an endoscope system and an endoscope system operation method that display a virtual scale for measuring the size of a subject.

2. Description of the Related Art

In endoscope systems including a light source device, an endoscope, and a processor device, the acquisition of a distance to a subject, the size of the subject, or the like is performed. For example, WO2018/051680A (corresponding to US2019/0204069A1) describes "an auxiliary light irradiation unit that irradiates a subject with auxiliary measurement light, an imaging unit that acquires an image of the subject on which a spot is formed by the auxiliary measurement light via an imaging optical system and an imaging element, a display device that displays the acquired image of the subject, and a processor that causes the display device to display, together with the image of the subject, an index figure showing the actual size of a specific region in the subject depending on whether the imaging unit acquires the image of the subject and having a size set depending on the position of the spot in the imaging element.

Additionally, WO2021/131238A (corresponding to US2022/0330850A1) describes "A processor acquires a captured image obtained by imaging a subject including a specific region formed on the subject by auxiliary measurement light, specifies the position of the specific region on the subject in the captured image, sets a reference scale indicating the actual size of the subject on the basis of the position of the specific region, extracts a region-of-interest included in the subject from the captured image, determines a measurement portion for measuring the size in the region-of-interest, generates a measurement value marker indicating a measurement value obtained by measuring the measurement portion of the region-of-interest on the basis of the reference scale, and creates a specific image in which the measurement value marker is superimposed on the captured image."

SUMMARY OF THE INVENTION

In WO2018/051680A and WO2021/131238A, the size of an object to be observed can be estimated by aligning a laser spot with the object to be observed, thereby comparing the index figure (virtual scale) with the object to be observed, such as the region-of-interest. However, a direction in which the virtual scale is displayed on an observation screen and a direction in which a user such as a doctor wants to measure the object to be observed do not necessarily coincide with each other. For this reason, in order to measure the object to be observed with the virtual scale on the observation screen, there is a case where it may take substantial time and effort for the user to have to operate the endoscope to cause the direction of the virtual scale to coincide with the direction in which the object is to be observed. Additionally, depending on the position of the object to be observed in a living body, there is a case where it may be difficult to operate the endoscope in the direction in which the object is to be observed. Moreover, in order to display the virtual scale in substantially real time in endoscopy, it is desired to speed up the processing up to the display of the virtual scale.

An object of the present invention is to provide an endoscope system and an endoscope system operation method capable of adjusting the display of a virtual scale in a direction in which an object to be observed is easy to measure, and displaying the virtual scale in substantially real time.

An endoscope system according to an aspect of the present invention comprises an imaging element that images a subject; a light source for auxiliary measurement light that emits auxiliary measurement light used for measuring the subject; and a processor. The processor is configured to acquire a captured image obtained by imaging the subject including a specific region formed by the auxiliary measurement light, specify a position of the specific region in the captured image, set a reference scale indicating an actual size of the subject on the basis of the position of the specific region, generate a display marker to be superimposed on the captured image on the basis of the reference scale, extract region-of-interest edge information from the captured image, detect a marker direction candidate position used for determining a display direction of the display marker on the basis of the region-of-interest edge information and specified distance position information indicating a distance from the position of the specific region, calculate a candidate distance, which is a distance from the position of the specific region to the marker direction candidate position, determine the marker direction candidate position, which forms the candidate distance equal to or larger than a specified distance from the position of the specific region, as a marker direction determination position, create a length measurement image in which the display marker that has the position of the specific region as a start point and passes through a part of an extension line passing through the marker direction determination position is superimposed on the captured image such that the position of the specific region is used as a base point, and display the length measurement image.

It is preferable that the specified distance position information is information indicating equal interval positions from the position of the specific region. It is preferable that the specified distance position information is concentric circles centered on the position of the specific region.

It is preferable that distortion of the specified distance position information is corrected. It is preferable that the specified distance position information is associated with size information indicating the actual size.

It is preferable that the processor is configured to set the specified distance position information, which is closest to the position of the specific region, in the specified distance position information as representative specified distance position information and associate the size information with the representative specified distance position information.

It is preferable that the display marker is a line segment having the position of the specific region as a base point and having the marker direction determination position as an end point, and the processor is configured to display a length of the actual size of the display marker, which is a distance from the position of the specific region to the marker direction determination position, on the basis of the size information.

It is preferable that the processor is configured to display a plurality of candidate markers as the display markers on the length measurement image in a case where a plurality of the marker direction determination positions are present.

It is preferable that the processor is configured to switch and display the plurality of candidate markers in the length measurement image.

It is preferable that the display marker consists of a plurality of line segments having the position of the specific region as a base point, and one of the plurality of line segments has the position of the specific region as a start point and includes an end point on the extension line that passes through the marker direction determination position.

It is preferable that the region-of-interest edge information is extracted by structure enhancement processing. It is preferable that the region-of-interest edge information is extracted using a trained model. It is preferable that the trained model is a convolutional neural network.

It is preferable that the processor is configured to generate a notification instruction by using the position of the specific region and the region-of-interest edge information to irradiate an end part of a region-of-interest with the auxiliary measurement light.

An endoscope system operation method according an another aspect of the present invention comprises a step of imaging a subject; a step of emitting auxiliary measurement light used for measuring the subject; a step of acquiring a captured image obtained by imaging the subject including a specific region formed by the auxiliary measurement light; a step of specifying a position of the specific region in the captured image; a step of setting a reference scale indicating an actual size of the subject on the basis of the position of the specific region; a step of generating a display marker to be superimposed on the captured image on the basis of the reference scale; a step of extracting region-of-interest edge information from the captured image; a step of detecting a marker direction candidate position used for determining a display direction of the display marker on the basis of the region-of-interest edge information and specified distance position information indicating a distance from the position of the specific region; a step of calculating a candidate distance, which is a distance from the position of the specific region to the marker direction candidate position; a step of determining the marker direction candidate position, which forms the candidate distance equal to or larger than a specified distance from the position of the specific region, as a marker direction determination position; a step of creating a length measurement image in which the display marker that has the position of the specific region as a start point and passes through a part of an extension line passing through the marker direction determination position is superimposed on the captured image such that the position of the specific region is used as a base point; and a step of displaying the length measurement image.

According to the present invention, it is possible to adjust the display of a virtual scale in a direction in which an object to be observed is easy to measure, and display the virtual scale in substantially real time.

BRIEF DESCRIPTION OF THE DRAWINGS

FIG. 1 is a schematic view of an endoscope system.
FIG. 2 is a plan view showing a distal end part of an endoscope.
FIG. 3 is a block diagram showing the functions of the endoscope apparatus.

FIG. 32 is an explanatory diagram showing an example of switching and displaying length measurement images in which candidate markers different from each other are displayed.

DESCRIPTION OF THE PREFERRED EMBODIMENTS

Figure 4:
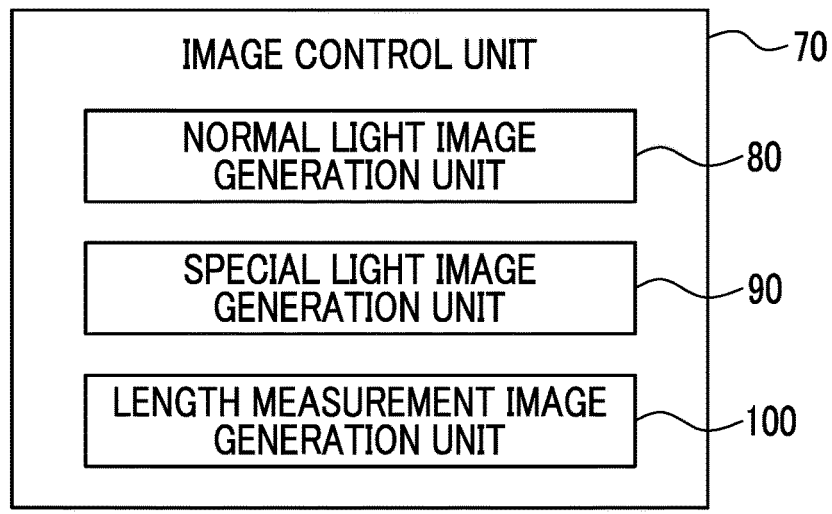
FIG. 4 is a block diagram showing the functions of a signal processing unit.

As shown in FIG. 1, an endoscope system 10 has an endoscope 12, a light source device 13, a processor device 14, a display 15, and a user interface 16. The endoscope 12 is optically connected to the light source device 13 and electrically connected to the processor device 14. The various connections are not limited to wired connections and may be wireless connections. Additionally, the connections may be performed via a network.

The endoscope 12 has an insertion part 12a to be inserted into the inside of a body, which is an object to be observed, an operating part 12b provided at a proximal end portion of the insertion part 12a, and a bendable part 12c and a distal end part 12d provided on a distal end side of the insertion part 12a. The bendable part 12c is operated in a bendable manner by operating an angle knob 12e of the operating part 12b. The distal end part 12d is directed in a desired direction by the bending operation of the bendable part 12c.

The distal end part 12d emits the illumination light toward the object to be observed and receives the reflected light from the object to be observed to image the object to be observed. A forceps channel (not shown) for inserting a treatment tool or the like may be provided from the insertion part 12a to the distal end part 12d. The treatment tool is inserted into the forceps channel through a forceps port 12j.

Additionally, the operating part 12b is provided with an observation mode selector switch 12f used for the switching operation of an observation mode, a still image acquisition instruction switch 12g used for giving an instruction on the acquisition of a still image of the object to be observed, and a zoom operation part 12h used for operating a zoom lens (not shown).

The processor device 14 is connected to the display 15 and the user interface 16. The display 15 outputs and displays a medical image (including a captured image, a specific region image, a normal light image, a special light image, and a length measurement image) processed by the processor device 14, information, and the like. The user interface 16 includes a keyboard, a mouse, a microphone, a speaker, a foot switch, a touch pad, a tablet, a touch pen, and the like and receives input operations such as function settings.

The endoscope 12 comprises a normal observation mode, a special observation mode, and a length measurement mode and is switched by the observation mode selector switch 12f. The normal observation mode is a mode in which the object to be observed is illuminated with normal light, which is illumination light having a wide band. The special observation mode is a mode in which the object to be observed is illuminated with a special light, which is illumination light having a narrow band different from the normal light. In the length measurement mode, the object to be observed is illuminated with the illumination light or the auxiliary measurement light, and a display marker as a virtual scale used for measuring the size of the object to be observed or the like is displayed on the captured image obtained by imaging the object to be observed. The length measurement image on which the display marker is superimposition-displayed, or the captured image (including the normal light image, the special light image, and the specific region image) on which the display marker is not superimposed and displayed is displayed on the display 15. In addition, a plurality of the displays 15 may be connected to the processor device 14, and the captured image and the length measurement image may be displayed on the different displays 15, respectively.

In addition, the normal light is the illumination light used for observing the entire object to be observed by giving brightness to the entire object to be observed. The special light is illumination light used for enhancing and observing a structure such as a gland duct structure or a blood vessel in the object to be observed. The auxiliary measurement light is light used for setting a reference scale for generating the display marker, determining a position or direction in which the display marker is displayed, and determining a base point of the display marker. Additionally, in the present embodiment, the virtual scale displayed on the length measurement image will be described, but an actual scale may be provided in an actual lumen such that the actual scale can be checked through the captured image or the length measurement image. In this case, it is conceivable that the actual scales are inserted via a forceps channel of the endoscope 12 and the actual scales are made to protrude from the distal end part 12d.

As a user operates the still image acquisition instruction switch 12g, a screen displayed on the display 15 is freeze-displayed and also emits an alert sound to the effect that the still image is acquired. Then, the still image of the subject image obtained before and after the operation timing of the still image acquisition instruction switch 12g is stored in an image saving unit 52 in the processor device 14. In addition, the image saving unit 52 is a nonvolatile memory such as a hard disc or a USB (Universal Serial Bus) memory. In a case where the processor device 14 can be connected to the network, the still image of the captured image may be saved in an image saving server (not shown) connected to the network instead of or in addition to the image saving unit 52.

In addition, a still image acquisition instruction may be given by using an operation device other than the still image acquisition instruction switch 12g. For example, a foot switch may be connected to the processor device 14, and a still image acquisition instruction may be given in a case where the user has operated the foot switch. Additionally, mode switching may be performed with a foot pedal. Additionally, a gesture recognition unit (not shown) that recognizes a user's gesture may be connected to the processor device 14, and in a case where the gesture recognition unit recognizes a specific gesture performed by the user, the still image acquisition instruction may be given. The mode switching may also be performed using the gesture recognition unit.

Additionally, a visual line input unit (not shown) provided near the display 15 may be connected to the processor device 14, and in a case where the visual line input unit recognizes that the user's visual line is within a predetermined region of the display 15 for a certain period of time or longer, the still image acquisition instruction may be given. Additionally, in a case where a voice recognition unit (not shown) is connected to the processor device 14 and the voice recognition unit recognizes a specific voice emitted from the user input via the microphone, the still image acquisition instruction or the mode switching may be performed. Additionally, an operation panel (not shown) such as a touch panel may be connected to the processor device 14, and in a case where the user performs a specific operation on the operation panel, the still image acquisition instruction or mode switching may be performed.

As shown in FIG. 2, the distal end part 12d of the endoscope 12 has a substantially circular shape and is provided with the objective lens 31 located closest to the subject side among optical members constituting the imaging optical system 44b of the endoscope 12 an illumination lens 32 for irradiating the subject with illumination light, an auxiliary measurement light lens 33 for illuminating the subject with auxiliary measurement light described below, and an opening 34 for projecting the treatment tool toward the subject, and an air and water supply nozzle 35 for performing air and water supply.

The optical axis Ax (refer to FIG. 7) of the imaging optical system 44b (refer to FIG. 3) into which the reflected light from the subject extends in a direction perpendicular to a paper surface. A vertical first direction D1 is perpendicular to the optical axis Ax, and a lateral second direction D2 is perpendicular to the optical axis Ax and the first direction D1. The objective lens 31 and the auxiliary measurement light lens 33 are arranged in the first direction D1.

As shown in FIG. 3, the light source device 13 comprises a light source unit 20 and a light source control unit 21. The light source unit 20 emits illumination light for illuminating the subject. The illumination light emitted from the light source unit 20 is incident on a light guide 22 and is radiated to the subject through the illumination lens 32.

The light source unit 20 is configured by, for example, a semiconductor light source such as a light emitting diode (LED) having a plurality of colors, a combination of a laser diode and a phosphor, or a xenon lamp or a halogen light source. For example, the light source unit 20 has LEDs such as a violet light emitting diode (V-LED) that emits violet light, a blue light emitting diode (B-LED) that emits blue light, a green light emitting diode (G-LED) that emits green light, and a red light emitting diode (R-LED) that emits red light. Additionally, the light source unit 20 includes an optical filter or the like for adjusting a wavelength range of light emitted by an LED or the like.

The light source control unit 21 controls the light source unit 20 on the basis of an instruction from the system control unit 60. The system control unit 60 also controls a light source 45a for auxiliary measurement light (refer to FIG. 5) of an auxiliary measurement light emission unit 45 in addition to instructing the light source control unit 21 about the light source control. In the case of the normal observation mode, the system control unit 60 emits the normal light from the light source unit 20 and controls to turn off the light source 45a for auxiliary measurement light. In the case of the special observation mode, the special light is emitted from the light source unit 20 to control to turn off the light source 45a for auxiliary measurement light. In the case of the length measurement mode, the system control unit 60 controls to turn on or off the respective light sources of the light source unit 20 that emits the normal light or the special light, and the light source 45a for auxiliary measurement light that emits the auxiliary measurement light.

The illumination optical system 44a includes an illumination lens 32, and the light from the light guide 22 is emitted to the object to be observed via the illumination lens 32. The imaging optical system 44b includes the objective lens 31, a zoom lens (not shown), and an imaging element 46. The reflected light from the object to be observed is incident on the imaging element 46 via the objective lens 31 and the zoom lens. Accordingly, a reflected image of the object to be observed is formed on the imaging element 46.

The zoom lens has an optical zoom function for enlarging or reducing the subject as a zoom function by moving between a telephoto end and a wide end. The optical zoom function can be switched on and off by the zoom operation part 12h (refer to FIG. 1) provided in the operating part 12b of the endoscope, and the subject is enlarged or reduced in a specific magnification ratio by further operating the zoom operation part 12h in a state in which the optical zoom function is ON.

The imaging element 46 is a color imaging sensor, which captures the reflected image of the subject to output an image signal. It is preferable that the imaging element 46 is a charge coupled device (CCD) imaging sensor, a complementary metal-oxide semiconductor (CMOS) imaging sensor, or the like. The imaging element 46 used in the present invention is a color imaging sensor for obtaining a red image, a green image, and a red image in three colors of red (R), green (G), and blue (B). The red image is an image output from a red pixel provided with a red color filter in the imaging element 46. The green image is an image output from a green pixel provided with a green color filter in the imaging element 46. The blue image is an image output from a blue pixel provided with a blue color filter in the imaging element 46. The imaging element 46 is controlled by the imaging control unit 47.

The image signal output from the imaging element 46 is transmitted to a CDS/AGC circuit 48. The CDS/AGC circuit 48 performs correlated double sampling (CDS) and auto gain control (AGC)) on the image signal that is an analog signal. The image signal that has passed through the CDS/AGC circuit 48 is converted into a digital image signal by an analog/digital (A/D) converter 49. The A/D-converted digital image signal is input to a processor device 14 via a communication interface (I/F) 50 (refer to FIG. 3).

In the processor device 14, a program related to various kinds of processing or control is incorporated in a program storage memory (not shown). The system control unit 60 configured by a processor operates a program embedded in the program storage memory to realize the functions of the reception unit 51, the display control unit 53, and the signal processing unit 70.

The reception unit 51 of the processor device 14 receives an image signal transmitted from the communication I/F 50 and transmits the image signal to the signal processing unit 70. The signal processing unit 70 has a built-in memory for temporarily storing the image signal received from the reception unit 51, and processes an image signal group which is a set of image signals stored in the memory. In addition, the control signal related to the light source control unit 21 may be directly transmitted to the system control unit 60.

As shown in FIG. 4, the signal processing unit 70 comprises a normal light image generation unit 80, a special light image generation unit 90, and a length measurement image generation unit 100. In a case where the normal observation mode is set, it is preferable that the normal light image generation unit 80 of the signal processing unit 70 performs color conversion processing, color enhancement processing, and structure enhancement processing on the captured image to obtain a normal light image. Since the normal light image is an image obtained on the basis of the normal light in which the violet light V, the blue light B, the green light G, and the red light R are emitted in a well-balanced manner, the normal light image is an image having a natural hue.

Meanwhile, in a case where the special observation mode is set, it is preferable that the special light image generation unit 90 of the signal processing unit 70 obtains a special light image by performing, on the captured image, the structure enhancement processing for enhancing the structure of a blood vessel or the like or color difference enhancement processing in which a color difference a normal portion and a lesion portion or the like in the object to be observed is expanded.

In a case where the length measurement mode is set, the imaging element 46 images the subject irradiated with the auxiliary measurement light, and the captured image (specific region image) including the specific region, which is a region irradiated with the auxiliary measurement light is input to the processor device 14 as the image signal. Hereinafter, in the length measurement mode, the image including the specific region and the captured image, which is a target on which the display marker is superimposed, will be referred to as the specific region image. The "captured image" in the claims includes the specific region image. In the length measurement mode, the specific region image is transmitted to the length measurement image generation unit 100 of the signal processing unit 70 to create the length measurement image in which the display marker is superimposed on the specific region image. Details about the generation of the length measurement image will be described below.

Additionally, in a case where the length measurement mode is set, the specific region image may be transmitted to the normal light image generation unit 80 to simultaneously obtain the normal light image including the specific region. Additionally, the specific region image may be transmitted to the special light image generation unit 90 to simultaneously obtain the special light image including the specific region.

The display control unit 53 controls to display the normal light image, the special light image, or the length measurement image created by the signal processing unit 70 on the display 15. The system control unit 60 controls the imaging element 46 via the imaging control unit 47 provided in the endoscope 12 and further controls the image saved in the image saving unit 52. The imaging control unit 47 controls the CDS/AGC 48 and the A/D 49 in accordance with the control of the imaging element 46 and further transmits information to the light source control unit 21.

Figure 5:
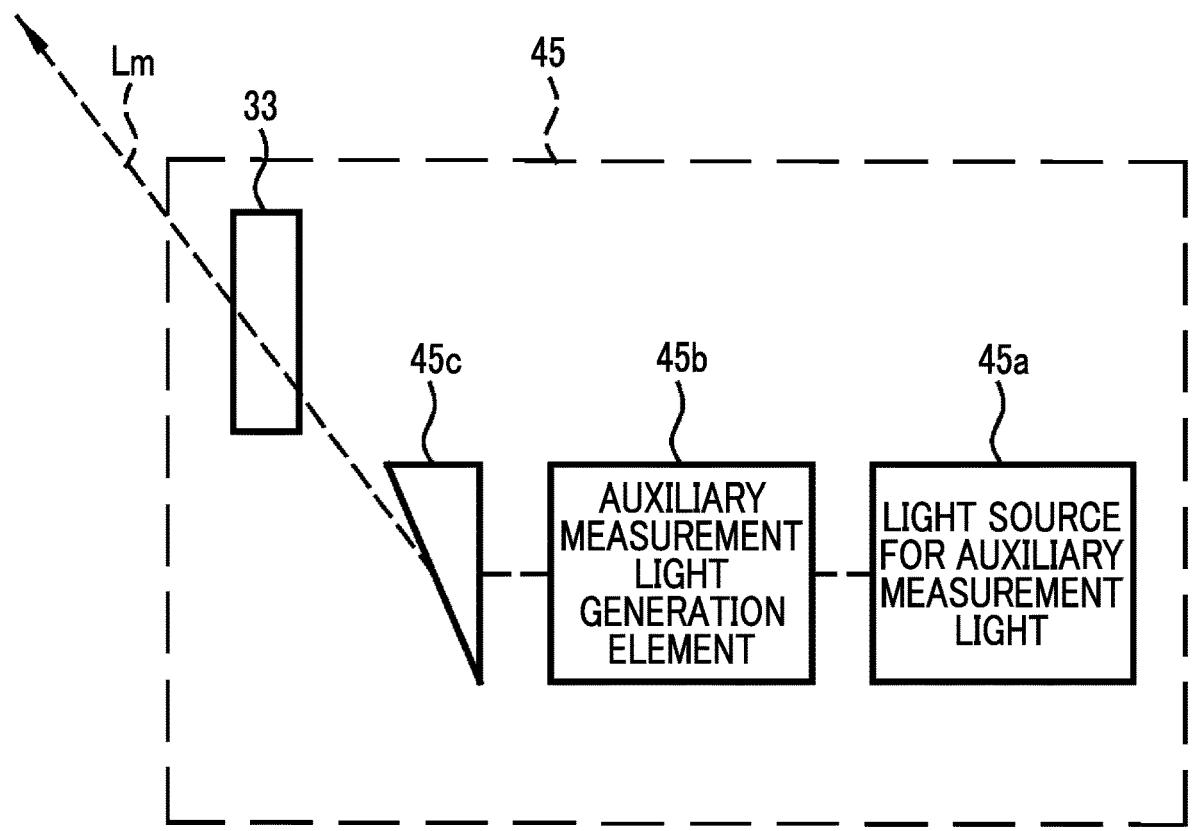
FIG. 5 is a block diagram showing the functions of an auxiliary measurement light emission unit.

As shown in FIG. 5, the auxiliary measurement light emission unit 45 emits the auxiliary measurement light obliquely with respect to the optical axis Ax (refer to FIG. 8) of the imaging optical system 44b. The auxiliary measurement light emission unit 45 comprises the light source 45a for auxiliary measurement light, an auxiliary measurement light generation element 45b, a prism 45c, and the auxiliary measurement light lens 33. The light source 45a for auxiliary measurement light emits spot-shaped auxiliary measurement light used for measuring the subject. The light source 45a for auxiliary measurement light emits light of a color (specifically, visible light) that can be detected by the pixels of the imaging element 46 and includes a light emitting element such as a laser light source laser diode (LD) or light-emitting diode (LED), a condenser lens that condenses the light emitted from the light emitting element.

It is preferable that the wavelength of the light emitted from the light source 45a for auxiliary measurement light is, for example, the red light of 600 nm or more and 650 nm or less. Alternatively, green light having a diameter of 495 nm or more and 570 nm or less may be used. The auxiliary measurement light generation element 45b converts the light emitted from the light source 45a for auxiliary measurement light into the auxiliary measurement light for obtaining the measurement information. Specifically, a collimator lens, a diffractive optical element (DOE), or the like is used as the auxiliary measurement light generation element 45b.

The prism 45c is an optical member for changing the traveling direction of the auxiliary measurement light after the conversion by the auxiliary measurement light generation element 45b. The prism 45c changes the traveling direction of the auxiliary measurement light so as to intersect the visual field of the imaging optical system 44b including the objective lens 31 and a lens group. The details of the traveling direction of the auxiliary measurement light will be described below. An auxiliary measurement light Lm emitted from the prism 45c is emitted to the subject through the auxiliary measurement light lens 33.

A spot (the specific region on the captured image) is formed on the subject by irradiating the subject with the auxiliary measurement light. The reception unit 51, which is an image acquisition unit, acquires the specific region image obtained by imaging the subject that is illuminated with the illumination light and has the spot formed with the auxiliary measurement light. The position of the specific region in the specific region image acquired by the reception unit 51 is specified by a position specifying unit 120 (refer to FIG. 8). A reference scale setting unit 130 sets the reference scale depending on the position of the specified specific region, and the display marker generation unit 140 sets an actual size representing the length measurement image on the basis of the reference scale. The generated display marker is superimposed on the captured image and displayed on the display 15 as the length measurement image.

Figure 6:
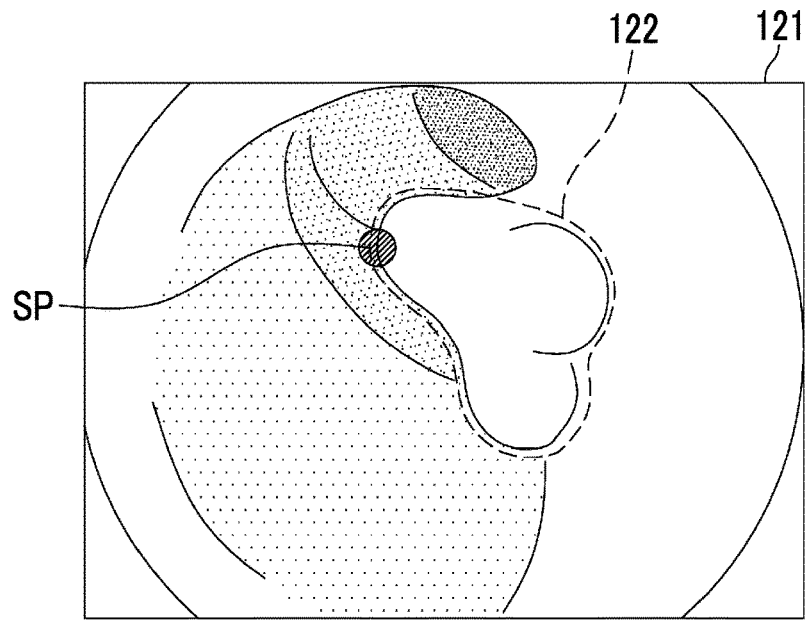
FIG. 6 is an image diagram of an example of a captured image including a subject on which a spot is formed.

As shown in FIG. 6, in a case where the auxiliary measurement light recognized by the specific region image 121 has a spot shape, the specific region is a spot SP of a circular region. The position specifying unit 120 (refer to FIG. 8) specifies the position of the spot SP in the specific region image as the specific region. In addition, it is preferable that the specific region image 121 shown in FIG. 6 is displayed on the display 15 from the timing at which the spot SP is irradiated in the length measurement mode to the timing at which the display marker is displayed. The captured image, which is the specific region image 121 shown in FIG. 6, includes a region-of-interest 122 in the subject. The region-of-interest will be described below.

In addition, instead of the auxiliary measurement light lens 33, a measurement assist slit may be provided at the distal end part 12d of the endoscope 12. Additionally, it is preferable that an anti-reflection coating (AR coating) (anti-reflection portion) is applied to the auxiliary measurement light lens 33. By providing the anti-reflection coating, the auxiliary measurement light is reflected without being transmitted through the auxiliary measurement light lens 33, it is possible to suppress a decrease in the ratio of the auxiliary measurement light with which the subject is irradiated, and prevent the position specifying unit 120 (refer to FIG. 8) from becoming difficult to recognize the position of the spot SP formed on the subject due to the auxiliary measurement light.

The auxiliary measurement light emission unit 45 may be any as long as the auxiliary measurement light emission unit 45 can emit the auxiliary measurement light toward the angle of view (visual field) of the imaging optical system 44b. For example, the light source 45a for auxiliary measurement light may be provided in the light source device 13 and the light emitted from the light source 45a for auxiliary measurement light may be guided to the auxiliary measurement light generation element 45b by an optical fiber or the like. Additionally, by installing the auxiliary measurement light source 45a and the auxiliary measurement light generation element 45b obliquely with respect to the optical axis Ax of the imaging optical system 44b without using the prism 45c, the auxiliary measurement light may be emitted in a direction crossing the visual field of the imaging optical system 44b.

Figure 7:
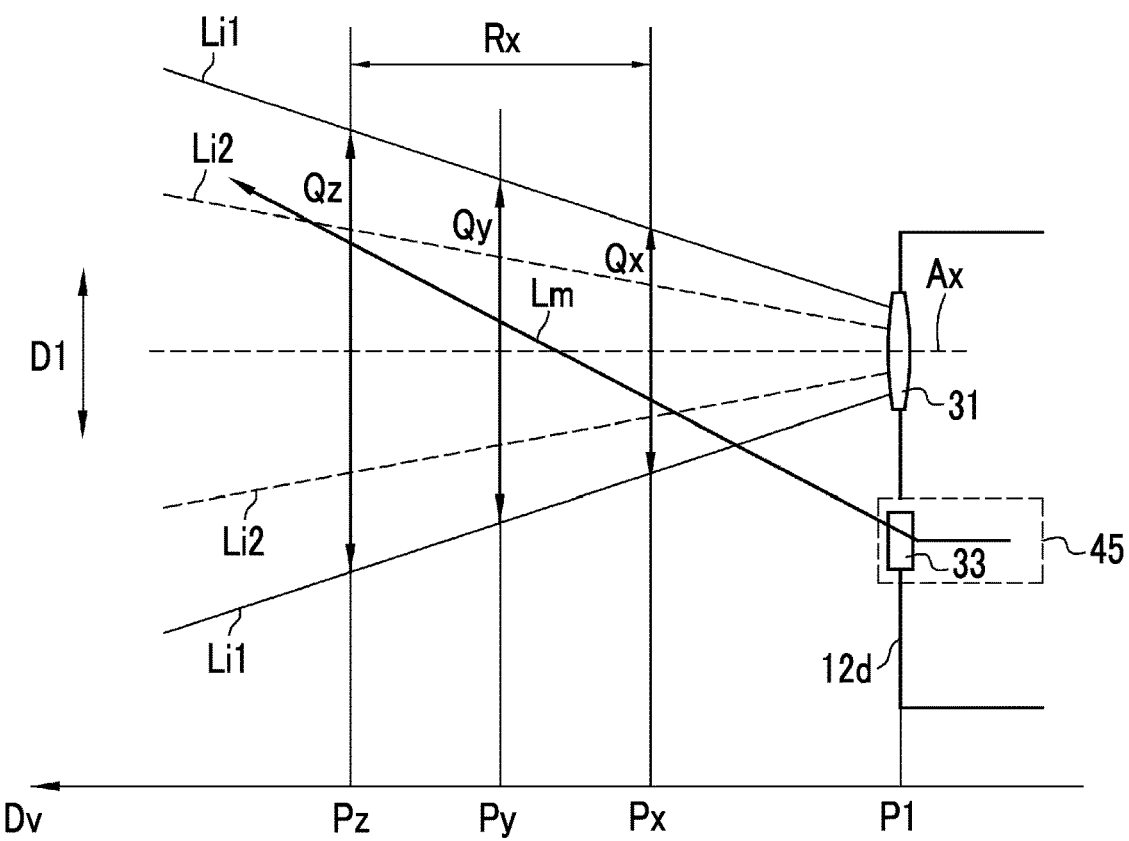
FIG. 7 is an explanatory diagram illustrating the position of the spot formed on the subject by auxiliary measurement light.

In a case where the auxiliary measurement light is emitted in the length measurement mode, the spot-shaped auxiliary measurement light is emitted in a state in which the traveling direction of the auxiliary measurement light intersects the optical axis Ax of the objective lens as shown in FIG. 7 and in a state in which the optical axis Lm of the auxiliary measurement light falls within an imaging angle of view (within a region sandwiched between two solid lines Li1) of the imaging optical system. Assuming that observation is possible in a range Rx of an observation distance, it can be seen that, in a near end Px, a center vicinity Py, and a far end Pz of the range Rx, the position (points where each of arrows Qx, Qy, and Qz intersect the optical axis Lm) of a spot SP formed on the subject by the auxiliary measurement light in an imaging range (indicated by each of the arrows Qx, Qy, and Qz) at each point are different from each other. The position of the distal end part 12d of the endoscope 12 is defined as a position P1. The observation distance is a distance between the distal end part 12d of the endoscope 12 and the subject. Therefore, the observation distance is a distance between the position P1 and the near end Px, the center vicinity Py, or the far end Pz, respectively. The observation distance is, in detail, a distance from a start point of the optical axis Ax of the imaging optical system 44b at the distal end part 12d of the endoscope 12 to the subject. An axis Dv indicates the observation distance. In addition, the imaging angle of view of the imaging optical system 44n is represented by the inside of a region sandwiched between two solid lines Li1, and the measurement is performed in a central region (a region sandwiched between two broken lines Li2) having less aberration in the imaging angle of view.

As described above, since the sensitivity of the movement of a spot position with respect to a change in the observation distance is high by emitting the auxiliary measurement light in a state of falling within the imaging angle of view of the imaging optical system, the size of the subject can be measured with high accuracy. By imaging the subject illuminated with the auxiliary measurement light with the imaging element 46, the captured image including the spot SP is obtained. In the captured image, the position of the spot SP varies depending on a relationship between the optical axis Ax of the imaging optical system 44b and the optical axis Lm of the auxiliary measurement light and the observation distance, but the number of pixels showing the same actual size (for example, 5 mm) increases in a case where the observation distance is shorter, and the number of pixels decreases in a case where the observation distance is longer. Therefore, by storing in advance the correspondence information (a scale table 131, refer to FIG. 8) in which the position of the spot SP and the measurement information (the number of pixels on the image) corresponding to the actual size of the subject are associated with each other, the reference scale can be set from the position of the spot SP, and the display marker generation unit 140 can generate the display marker.

Figure 8:
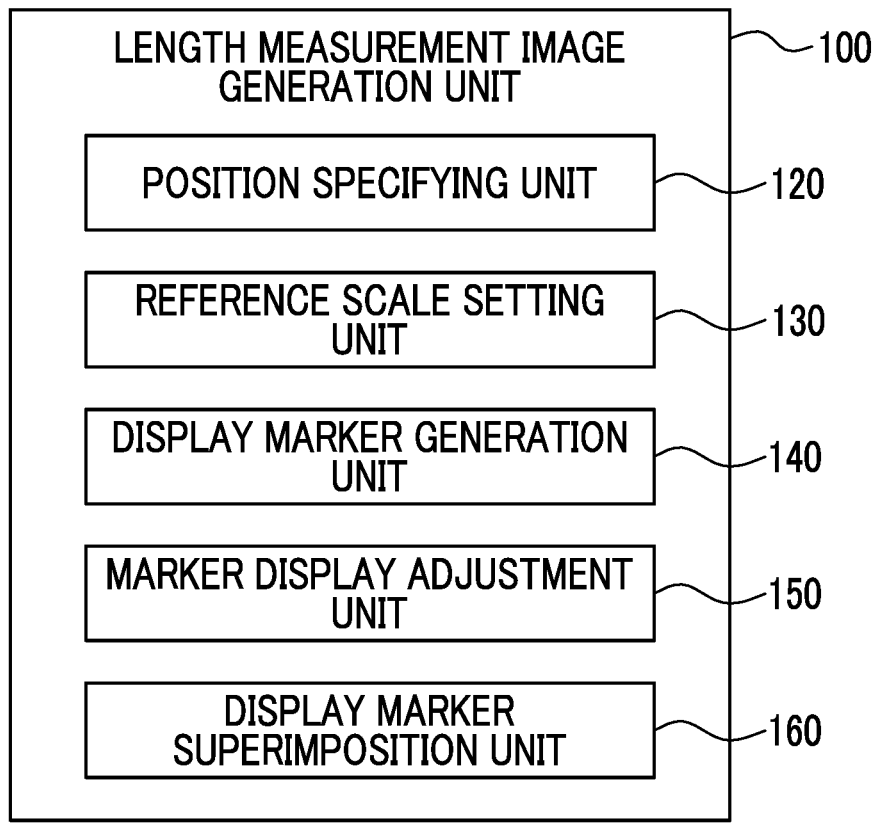
FIG. 8 is a block diagram showing the functions of a length measurement image generation unit.

As shown in FIG. 8, the length measurement image generation unit 100 of the signal processing unit 70 comprises the position specifying unit 120, the reference scale setting unit 130, the display marker generation unit 140, a marker display adjustment unit 150, and a display marker superimposition unit 160. The position specifying unit 120 specifies the position of the spot on the subject as the position of the specific region in the specific region image in order to perform setting or the like of the reference scale. The reference scale setting unit 130 sets a reference scale showing the actual size of the subject on the basis of the position of the specific region.

The display marker generation unit 140 further generates a display marker to be superimposed and displayed on the specific region image in accordance with the marker shape setting on the basis of the set reference scale. The marker display adjustment unit 150 determines a display direction in a case where the display marker is superimposed on the specific region image. Additionally, the preset display size is reflected in the display marker. The display marker superimposition unit 160 superimposes the display marker on the specific region image in accordance with the adjustment contents of the marker display adjustment unit 150 to generate the length measurement image. The generated length measurement image is transmitted to the display control unit 53 and displayed on the display 15.

In a case where the length measurement mode is set, the light source unit 20 and the auxiliary measurement light emission unit 45 continuously emit the illumination light and the auxiliary measurement light. In some cases, the auxiliary measurement light may be emitted by blinking or dimming. In addition, the captured image is an RGB image of three colors, but other color images (a brightness signal Y and color difference signals Cr and Cb) may be used.

The position specifying unit 120 specifies the position of the specific region. The position of the specific region is specified on the basis of the specific region image in which the subject is illuminated with the illumination light and the auxiliary measurement light in the length measurement mode. The specific region image of the subject on which the spot SP is formed by the auxiliary measurement light is acquired via the imaging optical system 44b and the imaging element 46.

It is preferable that the position specifying unit 120 recognizes the specific region from the image including a large number of components corresponding to the color of the auxiliary measurement light in the specific region image, and specifies the position as position information. The auxiliary measurement light is light that contains a large amount of a component of a specific color, for example, red. In a case where the specific color is red, it is preferable to specify the position of the specific region, which is the position of the spot SP formed on the subject, from the red image in the specific region image. In a method of specifying the position of the specific region, for example, there is a method of binarizing the red image of the specific region image and specifying the center of gravity of a black portion (pixels having a signal value higher than a position specification threshold) in the binarized image to the position of the specific region.

In addition, the specific color of the auxiliary measurement light may be another color, for example, green. In this case, the position of the specific region is specified from a green image in the specific region image. Additionally, the shape of the spot SP may be a circular shape, a polygonal shape including a star-shaped polygonal shape, or a star shape.

Figure 9:
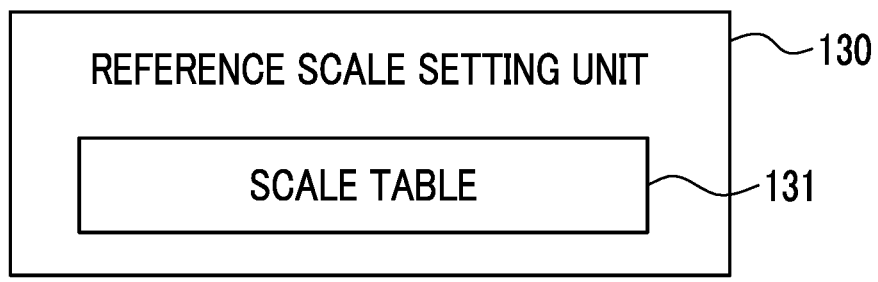
FIG. 9 is a block diagram showing the functions of a reference scale setting unit.

As shown in FIG. 9, the reference scale setting unit 130 comprises a reference scale table 131. The reference scale setting unit 130 sets a reference scale showing the actual size of the subject corresponding to the position of the specified specific region with reference to the scale table 131. The scale table 131 is correspondence information in which the position of the specific region and the measurement information corresponding to the actual size of the subject are associated with each other.

A method of creating the scale table 131 will be specifically described. For example, a relationship between the position of the specific region and the size of the marker (measurement information) can be obtained by imaging a chart in which a pattern of an actual size is regularly formed. Spot-shaped auxiliary measurement light is emitted toward the chart, a gridded chart with the same ruled lines (5 mm) as the actual size or finer ruled lines (for example, 1 mm) than the actual size is imaged while changing the observation distance to change the position of the spot, and a relationship between the position (pixel coordinates on the imaging surface of the imaging element 46) of the spot and the number of pixels (how many pixels the actual size of 5 mm is represented by) corresponding to the actual size is acquired.

Figure 10:
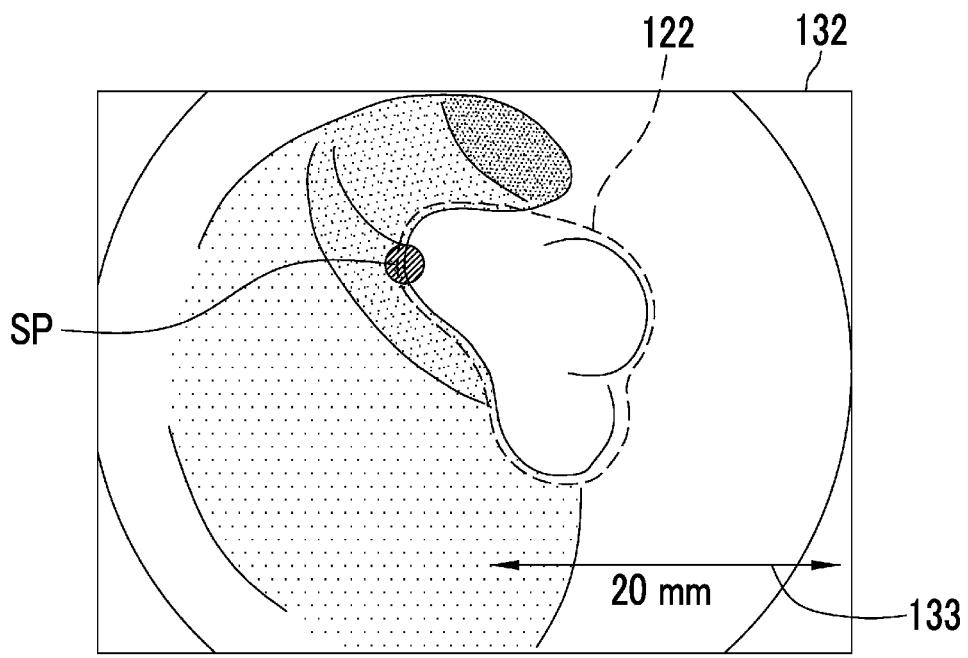
FIG. 10 is an image diagram showing an example of a length measurement image displayed by superimposing a reference scale.

The reference scale is a numerical value and a unit indicating the actual size and is information thereof, for example, a line segment having the number of pixels corresponding to 20 mm in the actual size. Normally, the reference scale is not displayed on the display 15, but the reference scale may be displayed on the display 15. In this case, for example, by providing the display marker generation unit 140 with a reference scale display function, as the length measurement image 132 as shown in FIG. 10, a reference scale 133 (the actual size is 20 mm in FIG. 10) may be superimposed on the specific region image and displayed on the display 15.

Figure 11:
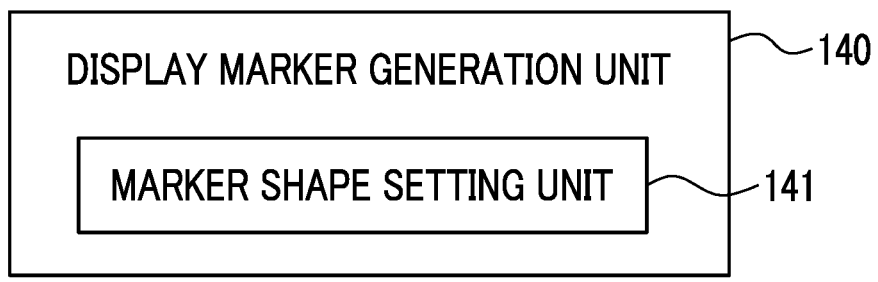
FIG. 11 is a block diagram showing the functions of a display marker generation unit.

The display marker generation unit 140 generates the display marker by receiving the information of the reference scale from the reference scale setting unit 130 or reading the information from the memory. The display marker is the virtual scale displayed on the length measurement image. As shown in FIG. 11, the display marker generation unit 140 comprises a marker shape setting unit 141 in which the marker shape setting is stored. The generated display marker is temporarily stored in the memory.

Figure 12:
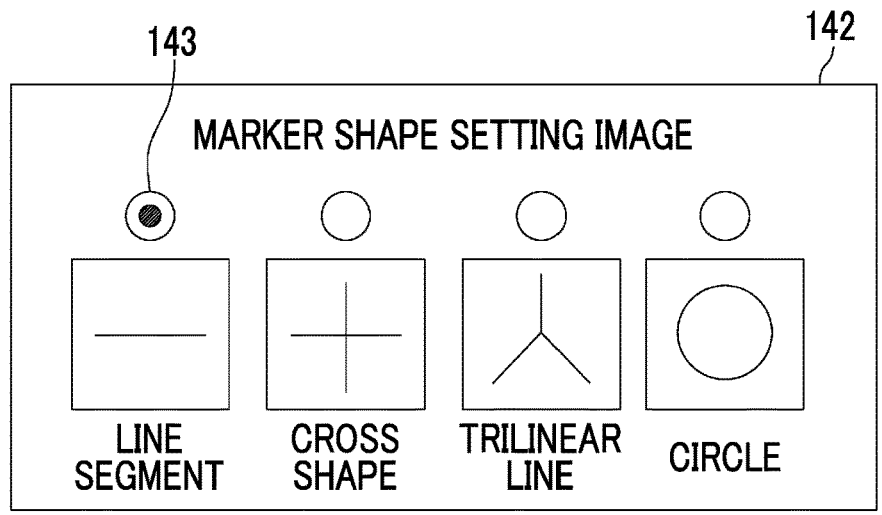
FIG. 12 is an image diagram showing an example of a marker shape setting image.

The marker shape setting unit 141 stores the marker shape setting that is selected by the user or is automatically set. In a case where the user is allowed to select the marker shape, the system control unit 60 may display the marker shape setting image 142 as shown in FIG. 12 on the display 15. In the marker shape setting image 142, any marker shape can be selected, for example, with a radio button 143. The marker shape includes, for example, a line segment, a cross shape, a trilinear shape, and a circular shape, and the marker shape is not limited thereto. In addition, the circular shape includes a perfect circle and an ellipse. Additionally, in the drawings, unless otherwise specified, the display marker is shown by a solid line, but the display marker may be displayed by a broken line. It may be possible to set whether to display the display marker displayed on the length measurement image as a solid line or a broken line, or it may be possible to set the color of the display marker.

Figure 13:
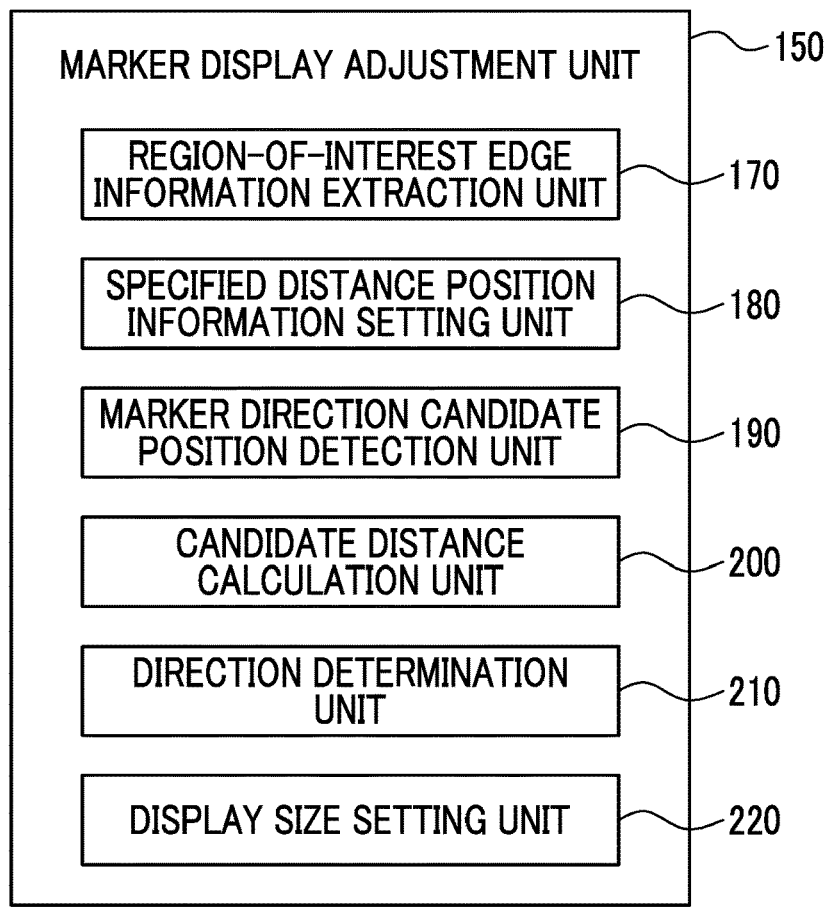
FIG. 13 is a block diagram showing the functions of a marker display adjustment unit.

As shown in FIG. 13, the marker display adjustment unit 150 comprises a region-of-interest edge information extraction unit 170, a specified distance position information setting unit 180, a marker direction candidate position detection unit 190, a candidate distance calculation unit 200, a direction determination unit 210, and a display size setting unit 220.

In the marker display adjustment unit 150, the marker direction candidate position detection unit 190 detects at least one or more marker direction candidate positions, using the region-of-interest edge information extracted by the region-of-interest edge information extraction unit 170 and the specified distance position information based on the setting read out by the specified distance position information setting unit 180. Next, the candidate distance calculation unit 200 calculates the candidate distance, which is the distance from the position of the specific region to the marker direction candidate position. Next, the direction determination unit 210 determines to display the display marker in the direction of the marker direction candidate position that forms a maximum candidate distance from the position of the specific region.

A base point of the display marker is the position of the specific region. The display marker superimposition unit 160 (refer to FIG. 8) uses the position of the specific region specified by the position specifying unit 120 for the superimposition-display of the display marker. The display size setting unit 220 sets and holds the display size of the display marker. The display marker superimposition unit 160 reads out the display size and uses the display size for the superimposition-display of the display marker.

The region-of-interest edge information extraction unit 170 of the marker display adjustment unit 150 extracts the region-of-interest edge information from the specific region image. An image transmitted from the reception unit 51 to the length measurement image generation unit 100 is used as the specific region image. The region-of-interest edge information is information obtained by extracting a portion corresponding to an end part of the region-of-interest of the subject from the specific region image.

The region-of-interest is a region to which the user included in the subject should pay attention. The region-of-interest is, for example, a region in which a lesion such as a polyp, a tumor, or inflammation is present, or a region in which a lesion is suspected to be present. By displaying the display marker on the length measurement image, an accurate actual size of the region-of-interest can be measured. The accurate actual size of the region-of-interest is useful for improving the accuracy of diagnosis. Additionally, the actual size of the region-of-interest is useful information in a case where the user or the like determines what kind of treatment is to be performed, and further selects an appropriate treatment tool for performing the treatment.

For example, the actual size of the polyp shown in the captured image is one of determination materials for determining whether to perform polypectomy or to adapt another treatment method in a scene in which the user or the like has found the polyp in the stomach or the large intestine. Additionally, in a case where a treatment such as polypectomy or endoscopic mucosal resection (EMR) is performed, it is possible to contribute to the selection of a polypectomy snare having a snare loop of an appropriate size by knowing the actual size of the region-of-interest during observation.

Figure 14:
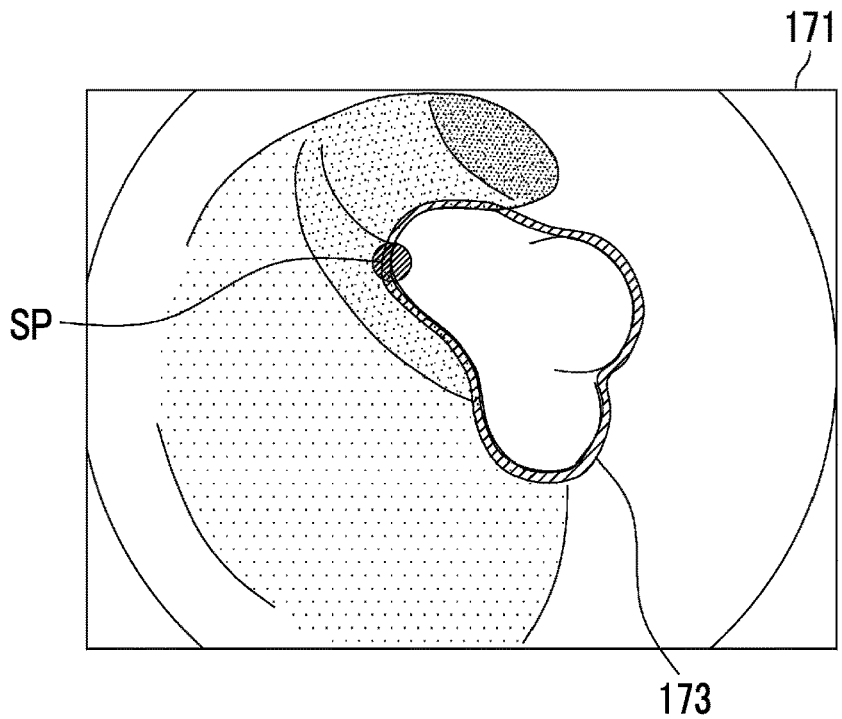
FIG. 14 is an image diagram showing an example in which region-of-interest edge information is shown on an image.

A specific example in which the region-of-interest edge information is extracted from the specific region image will be described. In the example shown in FIG. 14, the region-of-interest in a specific region image 171 in which the spot SP is formed is a polyp having a three-dimensional shape such that spheres overlap each other (refer to FIG. 6). As shown in FIG. 14, the region-of-interest edge information extraction unit 170 extracts the end part of the region-of-interest included in the specific region image 171 as region-of-interest edge information 173. The region-of-interest edge information 173 extracted in this way is transmitted to the marker direction candidate position detection unit 190.

The specified distance position information setting unit 180 reads out the setting related to the specified distance position information used for detecting the marker direction candidate position, which will be described below, and transmits the setting to the marker direction candidate position detection unit 190. The specified distance position information refers to information at a position separated from the position of the specific region by a certain specified interval from the position of the specific region in the specific region image. In the present embodiment, superimposing the specified distance position information on the specific region image is described as "setting the specified distance position information on the specific region image".

Figure 15:
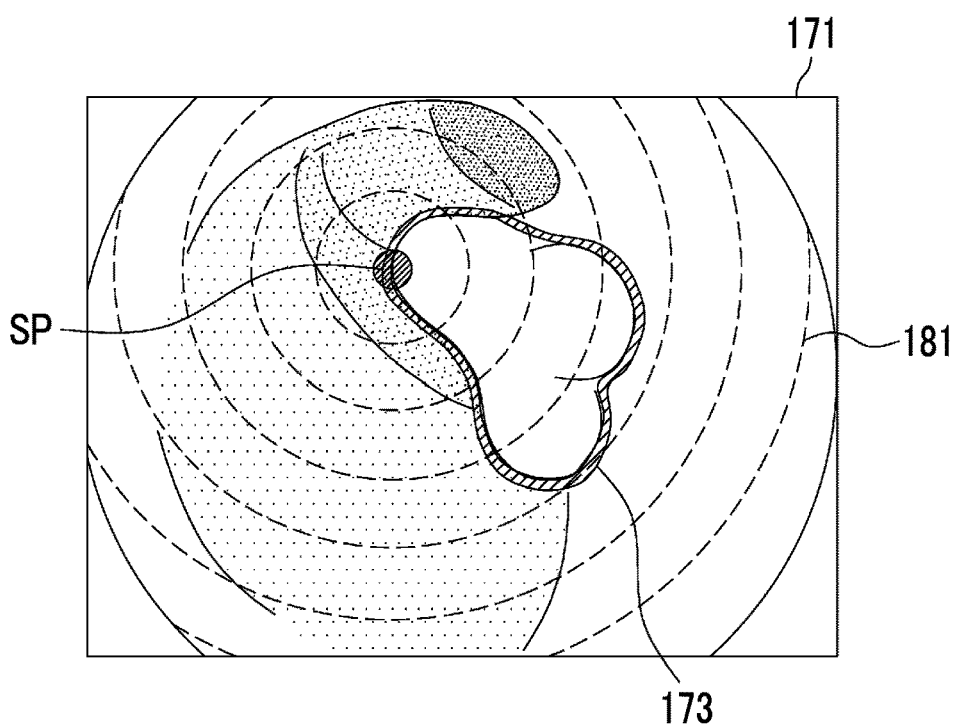
FIG. 15 is an image diagram showing an example in which specified distance position information of a perfect circle is shown on an image.

Specifically, the specified distance position information is information on positions separated at specified regular intervals from the position (indicated by the spot SP) of the specific region of the specific region image 171 designated as shown in FIG. 15. FIG. 15 shows specified distance position information 181 in which the loci of positions separated by a distance of regular intervals, which are equal intervals, are represented by a circle or an arc (dotted line). The specified distance position information setting unit 180 reads out a setting as to whether the specified distance position information 181 is represented by the number of pixels on the image in the specific region image 171 or is represented in an actual size accompanied by size information. In addition, in FIG. 15, the specified distance position information 181 farthest from the spot SP is designated as a representative by a leader line and a reference numeral. Additionally, as will be described below, it is preferable that the size information can be set to be associated only with representative concentric circles in the specified distance position information 181.

In a case where the specified distance position information is represented by the number of pixels, the specified distance position information is not accompanied by the information of the actual size. Additionally, in this case, the specified distance position information setting unit 180 reads out information on how many pixels the distance of the regular intervals is.

For example, in a case where the distance of the regular intervals, which are equal intervals, is 100 pixels, in FIG. 15, the specified distance position information 181 indicated by the innermost circle from the position (indicated by the spot SP) of the specific region indicates the loci of positions separated by 100 pixels. Similarly, the loci of positions separated by 100 pixels, such as 200 pixels, 300 pixels, and 400 pixels from the specified distance position information 181 indicated by the innermost circle, are exemplified as the specified distance position information 181.

Figure 16:
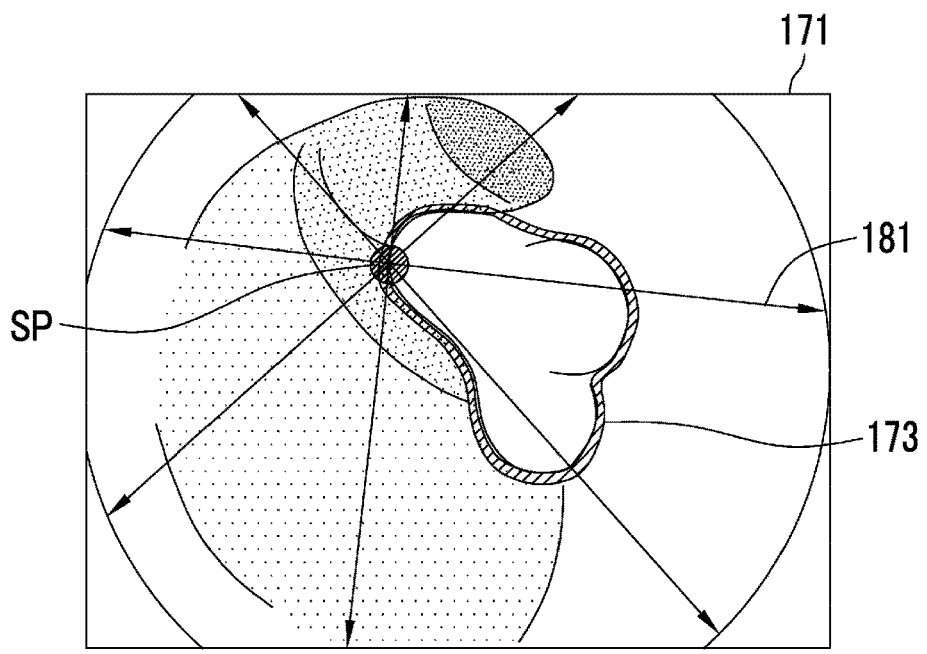
FIG. 16 is an image diagram showing an example in which linear specified distance position information is shown on an image.

The details will be described below, but the specified distance position information 181 is not limited to the shape of the perfect circle as shown in FIG. 15. For example, as shown in FIG. 16, the specified distance position information 181 indicated by a plurality of arrows that are drawn radially about the position (indicated by the spot SP) of the specific region in which the positions separated by 100 pixels are indicated by a scale may be used. In this case, the number of the specified distance position information 181 is not limited to eight, and it is preferable that the number of the specified distance position information 181 can be set as any number.

In a case where the specified distance position information is represented in the actual size, the size information output by the reference scale setting unit 130 and the specified distance position information are associated with each other. The size information refers to information on the reference scale (a correspondence relationship between the number of pixels and the actual size). In this case, the specified distance position information setting unit 180 reads out information on how many millimeters the distance of the regular intervals is. The unit of the distance of the regular intervals is not limited to millimeters. For example, the unit may be a centimeter, micrometer, or nanometer.

Using the example shown in FIG. 15, in a case where the distance of the regular intervals, which are equal intervals, is 10 millimeters, the specified distance position information 181 indicated by the innermost circle from the position (indicated by the spot SP) of the specific region indicates the loci of positions separated by 10 millimeters. Similarly, the loci of positions separated by 10 mm, such as 20 mm, 30 mm, and 40 mm from the specified distance position information 181 indicated by the innermost circle, serve as the specified distance position information.

In addition, the specified distance position information may be information on a distance of regular intervals that gradually increase or decrease, in addition to the equal interval intervals as shown in FIG. 15. For example, the specified distance position information can be information on intervals (gradually interval-increased position information) that gradually increase at regular intervals. In this case, the specified distance position information gradually increases every 100 pixels, for example.

Figure 17:
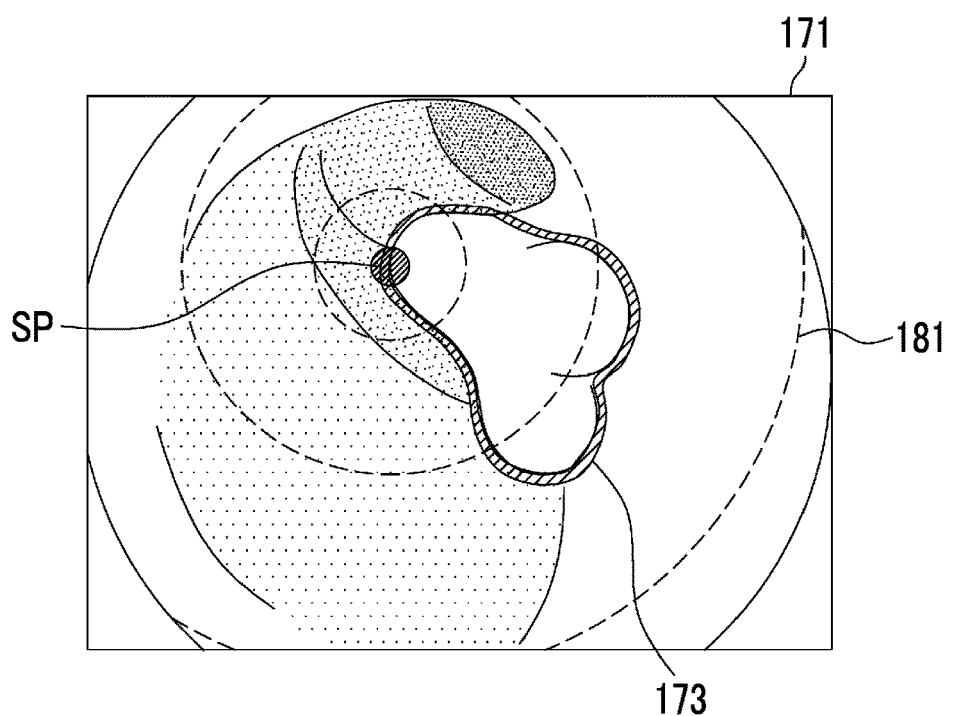
FIG. 17 is an image diagram showing an example in which gradually interval-increased position information is shown on an image.

Specifically, as shown in FIG. 17, the specified distance position information 181 indicated by the innermost circle from the position (indicated by the spot SP) of the specific region indicates a locus of a position 100 pixels away from the position of the specific region, and the specified distance position information 181 indicated by one outer circle is a locus of a position 300 pixels away from the spot SP. The specified distance position information 181 indicated by one more outer circle is a locus of a position 600 pixels away from the spot SP. That is, the specified distance position information 181 shown in FIG. 17 is the specified distance position information 181 in which the regular intervals are gradually increased by 100 pixels, 200 pixels, or 300 pixels from the spot SP. By setting the specified distance position information as the gradually interval-increased position information, the specified distance position information can be set to a wide range of the specific region image. In particular, the specified distance position information is useful in a case where the region-of-interest is present in a wide range of the specific region image, such as in a case where high-magnification observation is performed.

Additionally, in a case where the specified distance position information is set as information (gradually interval-decreased position information) on intervals that gradually decrease at regular intervals, the specified distance position information gradually increases every 100 pixels, for example.

Figure 18:
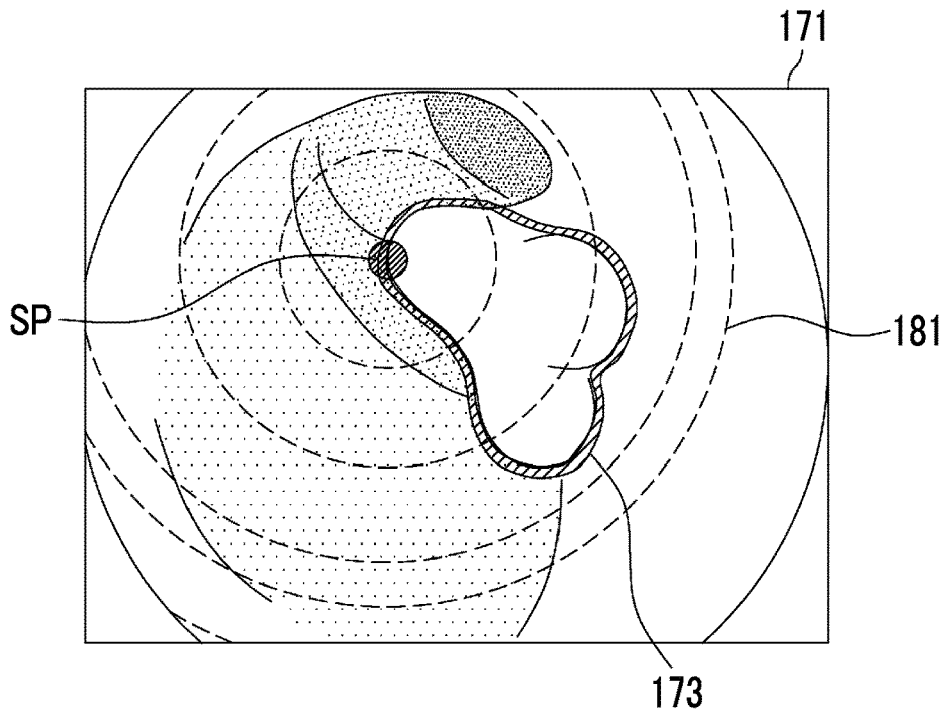
FIG. 18 is an image diagram showing an example in which gradually interval-decreased position information is shown on an image.

Specifically, as shown in FIG. 18, the specified distance position information 181 indicated by the innermost circle from the position (indicated by the spot SP) of the specific region indicates a locus of a position 150 pixels away from the position of the specific region, and the specified distance position information 181 indicated by one outer circle is a locus of a position 300 pixels away from the spot SP. Similarly, the specified distance position information 181 indicated by one more outer circle is a locus of a position 450 or 500 pixels away from the spot SP. That is, the specified distance position information 181 shown in FIG. 18 is the specified distance position information 181 in which the regular intervals are gradually decreased by 150 pixels, 300 pixels, 450 pixels, or 500 pixels from the spot SP. By setting the specified distance position information as the gradually interval-decreased position information, the specified distance position information can be set to a narrow range of the specific region image. In particular, the specified distance position information is useful in a case where the region-of-interest is present in a wide range of the specific region image, such as in a case where low-magnification observation is performed.

It is preferable that the setting as to whether the specified distance position information is represented by any of the number of pixels or the actual size, and the setting as to the distance of the regular intervals can be performed automatically or optionally. In a case where the user sets the specified distance position information, a specified distance position information setting image (refer to FIGS. 15 to 18) may be displayed on the display 15, and the distance of the regular interval distance in a case where the regular intervals are set as an equal distance or the width of gradual increase or decrease of the regular intervals may be set The marker direction candidate position detection unit 190 detects the marker direction candidate position used for determining the display direction of the display marker by using the region-of-interest edge information and the specified distance position information. The marker direction candidate position detection unit 190 receives the information on the position of the specific region from the position specifying unit 120 or reads out the information from the memory. Additionally, the specified distance position information is received from the specified distance position information setting unit 180 or is read out from the memory.

Figure 19:
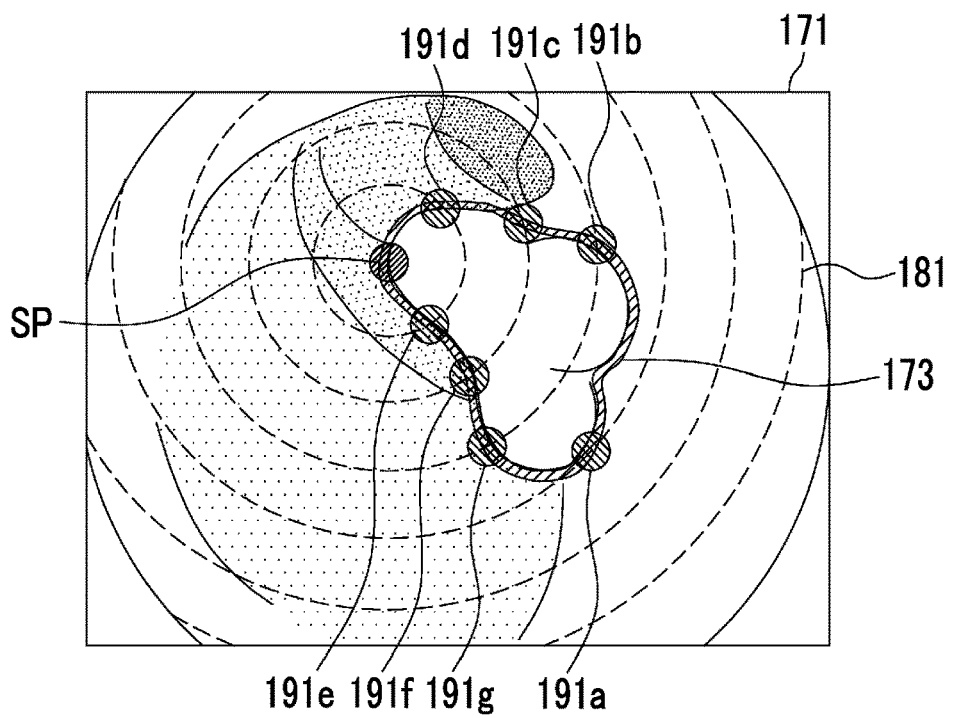
FIG. 19 is an image diagram showing an example in which marker direction candidate positions are shown on an image.

A specific method of detecting the marker direction candidate position will be described. The marker direction candidate position detection unit 190 detects intersection points where the region-of-interest edge information 173 extracted from the specific region image 171 and the specified distance position information 181 overlap each other, as shown in a specific example of FIG. 19, as marker direction candidate positions 191a, 191b, 191c, 191d, 191e, 191f, and 191g. In FIG. 19, the seven detected marker direction candidate positions 191a, 191b, 191c, 191d, 191e, 191f, and 191g are coordinate information in the specific region image 171.

Although FIG. 19 shows the region-of-interest edge information 173 and the specified distance position information 181 in the specific region image 171 for helping to understand, the information is actually coordinate information processed inside the processor device 14. In addition, the specified distance position information image in which the region-of-interest edge information 173 and the specified distance position information 181 can be confirmed as shown in FIG. 19 may be generated and displayed on the display 15.

Figure 20:
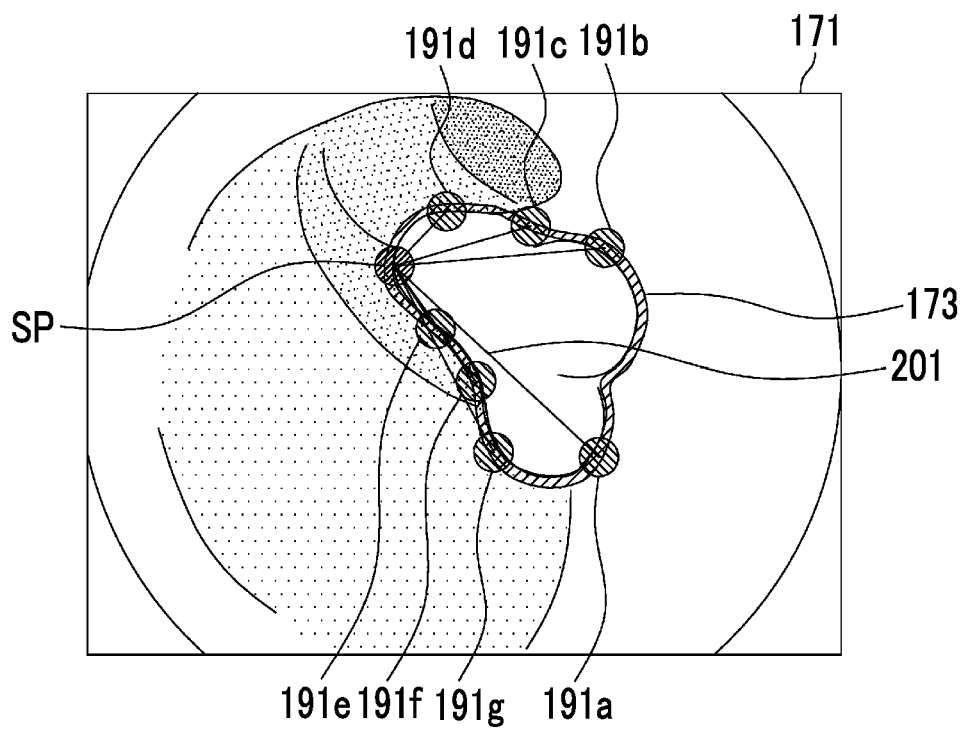
FIG. 20 is an image diagram showing an example in which candidate distances are shown on an image.

The candidate distance calculation unit 200 calculates the candidate distance, which is the distance from the position of the specific region to the marker direction candidate position. Specifically, as shown in FIG. 20, a candidate distance 201, which is the distance of each of the marker direction candidate positions 191a, 191b, 191c, 191d, 191e, 191f, and 191g from the spot SP, is calculated. In FIG. 20, the candidate distance 201 from the spot SP to the marker direction candidate position 191a is designated as a representative by a leader line and a reference numeral.

It is preferable that the candidate distance 201 is calculated from the specified distance position information. For example, in FIGS. 19 and 20, in a case where the specified distance position information indicates the position of an equal distance every 100 pixels, the candidate distance from the marker direction candidate position 191a is 400 pixels, and the candidate distance from the marker direction candidate positions 191b and 191g is 300 pixels, the candidate distance from the marker direction candidate positions 191c and 191f is 200 pixels, and the candidate distance from the marker direction candidate positions 191d and 191e is 100 pixels.

The direction determination unit 210 refers to a plurality of candidate distances calculated by the candidate distance calculation unit 200 and a preset specified distance and determines a marker direction candidate position having a candidate distance equal to or larger than the specified distance from the position of the specific region (the position of the spot SP) as the marker direction determination position. It is preferable that the specified distance is set optionally or automatically. Among the calculated candidate distances, a maximum one (maximum candidate distance) may be set as the specified distance.

In the specific example shown in FIG. 20, the candidate distance 201, which is the maximum candidate distance, is designated by a leader line and a reference numeral. In a case where the maximum candidate distance is set as the specified distance, the direction determination unit 210 determines the marker direction candidate position 191a as the marker direction determination position. The marker direction determination position is coordinate information for determining the end point direction of a display marker having the position of the specific region as a base point. That is, the display direction of the display marker is determined by the marker direction determination position determined by the direction determination unit 210.

In addition, the specified distance position information is numbered in short-distance order from the position of the specific region and set as Nth specified distance position information (N is a natural number), and the specified distance may be set as a distance from the position of the specific region to Mth specified distance position information. For example, in the specific example shown in FIG. 20, in a case where the specified distance is the fourth specified distance position information, the marker direction determination position is the marker direction candidate position 191*a*. In a case where the specified distance is the third specified distance position information, the marker direction determination positions are the marker direction candidate positions 191*a*, 191*b*, and 191*g*. A display method for the display marker in a case where a plurality of marker direction determination positions are present will be described below.

Figure 21:
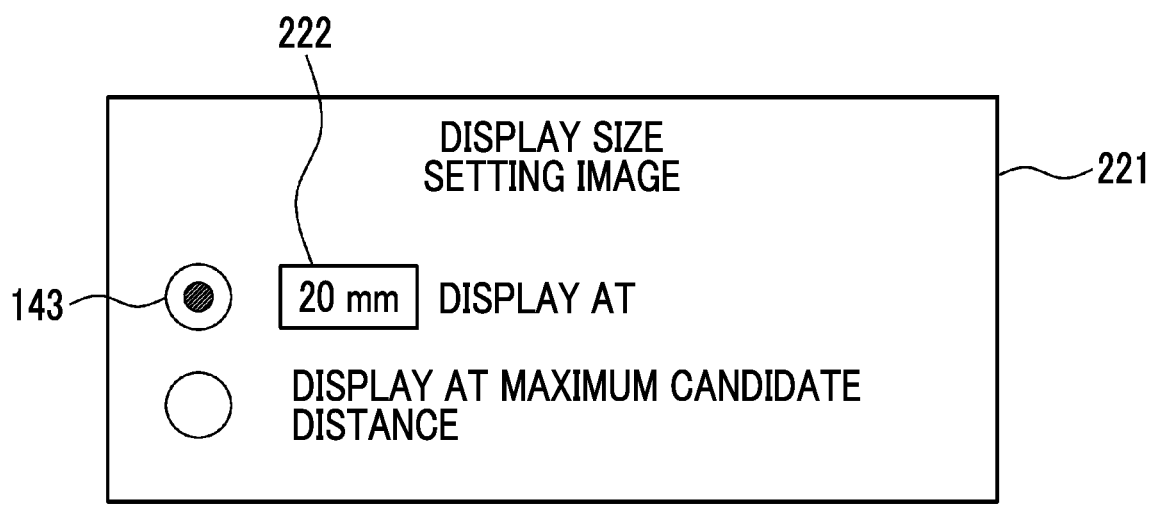
FIG. 21 is an image diagram showing an example of a display size setting image.

The display size setting unit 220 reads out the setting of the display size of the display marker. Examples of the display size setting include a specific example shown in FIG. 21. A display size setting image 221 shown in FIG. 21 is adapted such that "DISPLAY AT 20 mm" or "DISPLAY AT MAXIMUM CANDIDATE DISTANCE" can be selected for the display marker.

It is preferable that the display size of the display marker superimposed on the specific region image can be set optionally. For example, the display size of the display marker is changed by inputting an optional numerical value in a display size input field 222 of the display size setting image 221. Additionally, the unit (for example, centimeter, micrometer, or nanometer) of the display size may be set.

The display marker superimposition unit 160 superimposes the display marker having the position of the specific region as the base point on the specific region image so as to pass through at least an extension line passing through coordinates indicated by the marker direction determination position in the display size read out by the display size setting unit 220, and generates a length measurement image. The generated length measurement image is transmitted to the display control unit 53 and displayed on the display 15.

A specific example in which the display marker is superimposed and displayed in the actual size will be described. For example, the display size is set to "DISPLAY AT 20 mm". In this case, in the example of the length measurement image 230 shown in FIG. 22, a display marker 232 is displayed, which is a line segment, having an actual size of 20 mm, in which the display direction thereof is adjusted so as to face the direction of the marker direction determination position 231 (marker direction candidate position 191*a* in FIG. 20) with the position of the spot SP as the base point. The display marker 232 is superimposed and displayed so as to pass through at least a part of an extension line 233 (some of the coordinates of points constituting the extension line 233) that passes through the marker direction determination position 231 with the position of the specific region (the position of the spot SP) as a start point.

Figure 22:
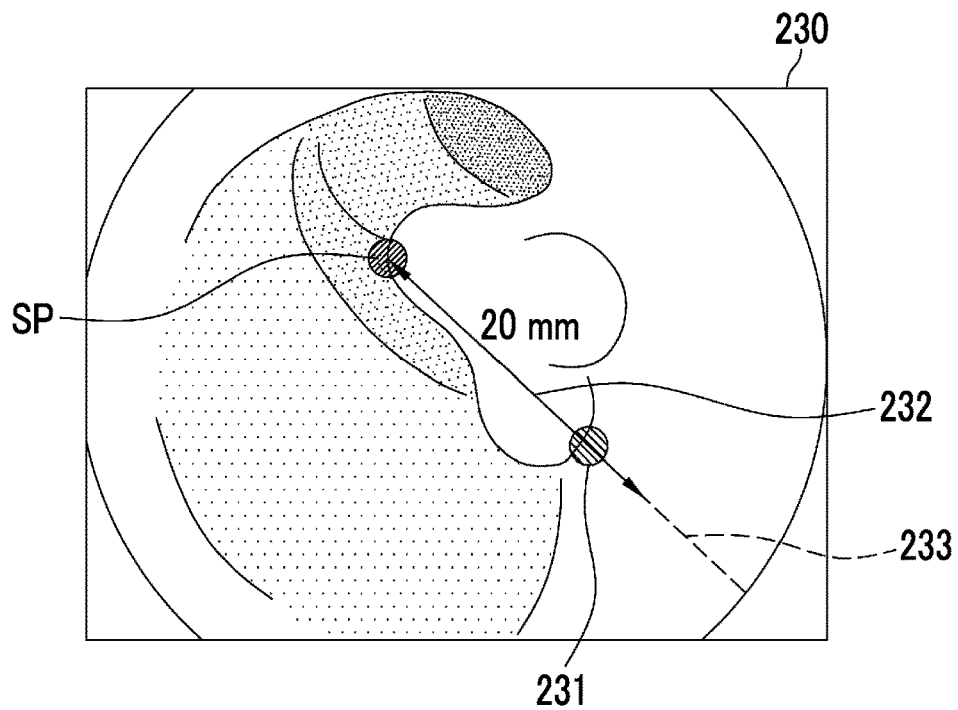
FIG. 22 is an image diagram showing an example of a length measurement image in which display markers are displayed in a case where the display markers are superimposed and displayed in a set size.
Figure 23:
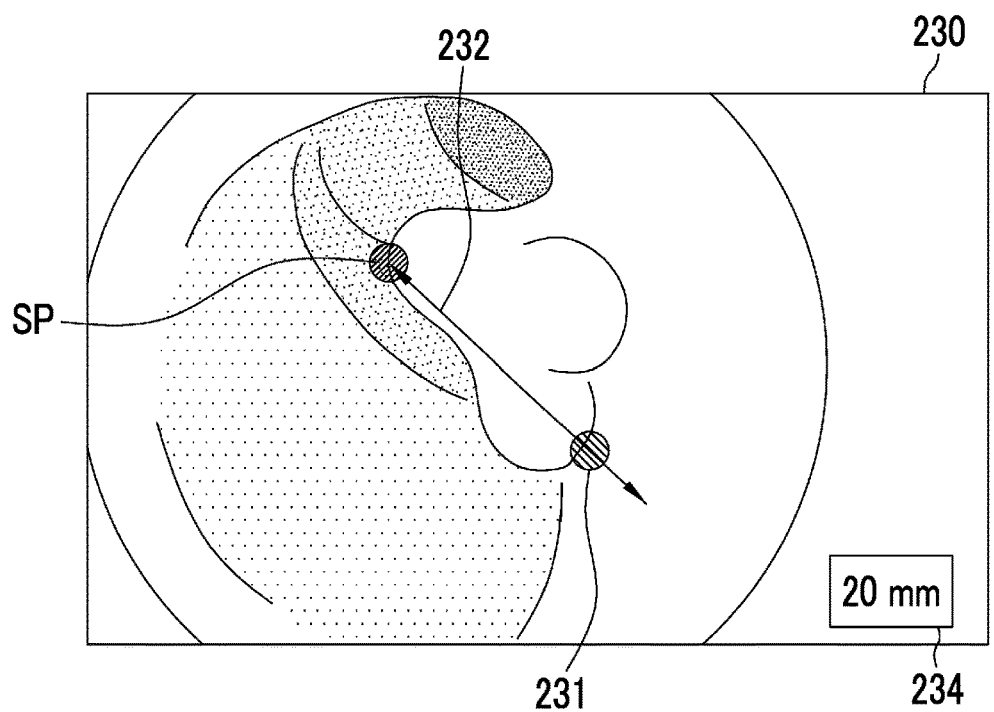
FIG. 23 is an image diagram showing an example of a length measurement image provided with a marker size display field.

The actual size of the display marker 232 may be displayed in the vicinity of the display marker 232 as shown in FIG. 22, or may be displayed as a marker size display field 234 that is not covered with the subject as shown in FIG. 23. By displaying the actual size in the vicinity of the display marker, the actual size of the region-of-interest that is being observed can be confirmed in the vicinity of the spot SP. On the other hand, by displaying the actual size so as not to be covered with the subject, the user can observe the length measurement image excluding information as much as possible, and can confirm the actual size only as necessary.

By virtue of the above configuration, it is possible to display the virtual scale in accordance with the size of the region-of-interest without operating the endoscope 12 in accordance with the direction of the fixed virtual scale. By automatically determining the display direction, for example, even in a situation where observation is difficult by being physically obstructed by a structure in a living body, such as pleats or a large lesion of the large intestine, it is realized that the display direction of the virtual scale is automatically adjusted in accordance with the direction of the maximum size of the region-of-interest observed in the captured image without moving the endoscope 12 in accordance with the fixed display position of the virtual scale.

Moreover, in a method in which the candidate distance is obtained only from the region-of-interest edge information, it is not determined which portion of the coordinate information in the region-of-interest edge information is used to calculate the candidate distance. Thus, the amount of calculation of the candidate distance becomes enormous. On the other hand, in the method of the present embodiment in which the edge information and the specified distance position information are combined with each other, it is sufficient to detect marker direction candidate positions that are candidates for direction determination and to calculate the candidate distances by the number of the marker direction candidate positions. For this reason, by further combining the specified distance position information to detect the marker direction candidate positions rather than calculating a large amount of candidate distances only from the edge information, the calculation of the candidate distances can be increased in speed, and the display direction of the display marker can be determined quickly. By virtue of such a configuration, it is possible to realize the display of the virtual scale in substantially real time during endoscope observation.

Figure 24:
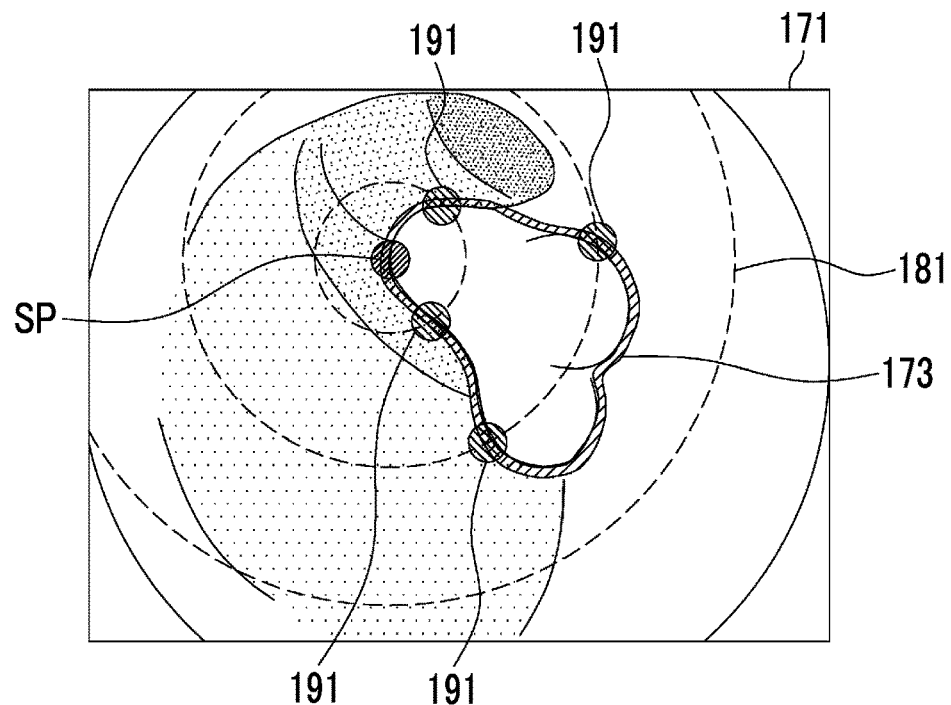
FIG. 24 is an image diagram showing an example in which the specified distance position information in a case where a distance of regular intervals is large is shown on an image.

The calculation speed can be further increased by increasing the distance of the regular intervals of the specified distance position information, that is, reducing the number of the specified distance position information. As illustrated in FIG. 24, in a case where the distance of the regular intervals of the specified distance position information 181 is increased as compared to the specific example of FIG. 15, the number of marker direction candidate positions 191 is reduced. For this reason, since the number of calculated candidate distances is also reduced, it is possible to shorten the time until the display direction of the display marker is determined.

On the other hand, in a case where the distance of the regular intervals of the specified distance position information is reduced, that is, in a case where the number of the specified distance position information is increased, the calculation takes a substantial time, but the accuracy of adjusting the display direction of the display marker can be improved. In summary, the calculation speed is increased in a case where the number of marker direction candidate positions is small, and the adjustment accuracy is increased in a case where the number of marker direction candidate positions is large.

It is preferable that the specified distance position information is information indicating equal interval positions from the position of the specific region. As shown in FIG. 15, by setting the specified distance position information at positions separated by the distance of the regular intervals, which are equal intervals from the position of the specific region, the display direction of the display marker can be determined quickly and accurately regardless of the imaging magnification of the specific region image.

It is preferable that the specified distance position information is concentric circles centered on the position of the specific region. That is, as shown in FIG. 15, it is preferable that the specified distance position information is concentric circles showing the loci of the positions separated by the distance of the regular intervals with the position of the specific region as a center. In a case where the specified distance position information is a line, there is a possibility that the number of marker direction candidate positions is too large or too small depending on the number of lines. For this reason, by making the specified distance position information concentric circles, the display direction can be adjusted with stable accuracy.

It is preferable that the marker direction candidate position detection unit 190 detects the marker direction candidate position by using the specified distance position information in which distortion is corrected. In this case, the marker direction candidate position detection unit 190 may read out the predetermined distance position information in which the distortion is corrected depending on the distance of the regular intervals, which is stored in advance, and the distortion correction of the specified distance position information 181 may be performed using the distortion correction chart image 185 stored in the image saving unit 52.

Figure 25:
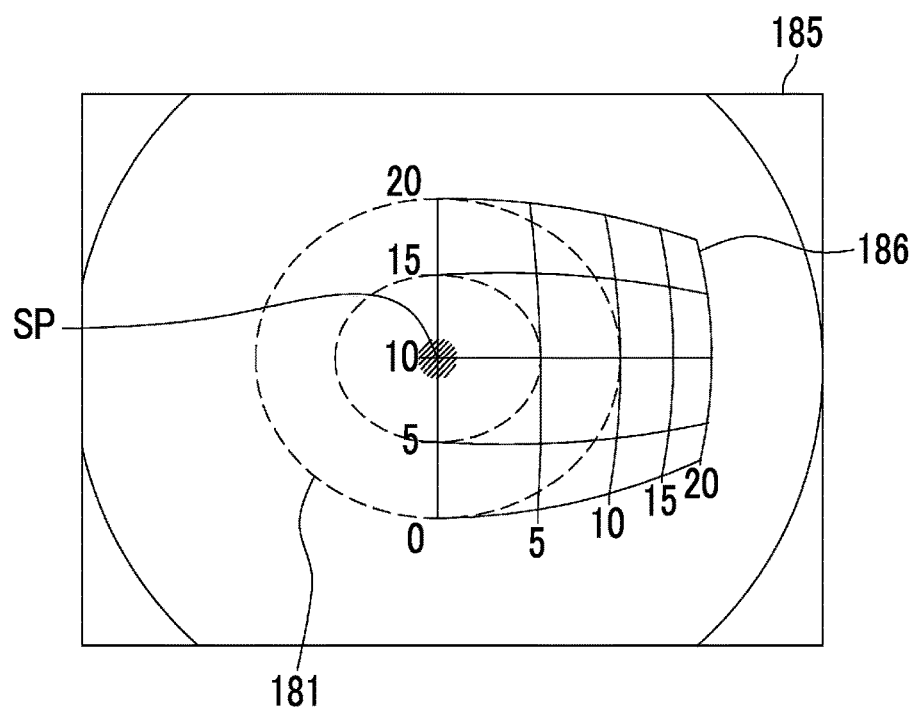
FIG. 25 is an image diagram showing an example of a distortion correction chart image.

The distortion correction chart image 185 can be obtained by imaging a chart 186 in which a pattern of the actual size is regularly formed, as shown in FIG. 25, using the endoscope 12. As the chart 186 in the distortion correction chart image 185 is deflected in a case where the reflected light incident on the endoscope 12 is transmitted through the objective lens 31, distortion occurs as compared to an actual image. As shown in FIG. 25, the specified distance position information setting unit 180 may set the specified distance position information 181 by using the distortion correction chart image 185 or may read out a distortion correction arithmetic expression obtained from a correspondence relationship between the chart 186 in the distortion correction chart image 185 and the coordinate deviation from a virtual chart having no distortion and set the specified distance position information in which the distortion is corrected.

Figure 26:
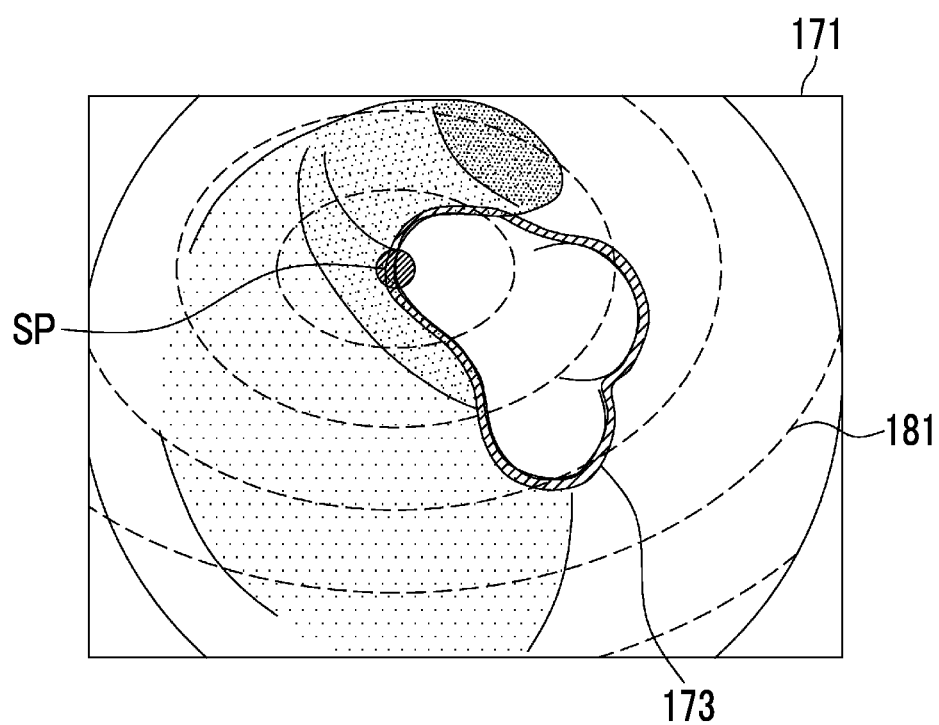
FIG. 26 is an image diagram showing an example in which distortion-corrected specified distance position information is shown on an image.

In a case where the distortion of the specified distance position information is corrected and the specified distance position information 181 is concentric circles, the specified distance position information 181 set in the specific region image 171 becomes an elliptical shape as shown in FIG. 26.

Figure 27:
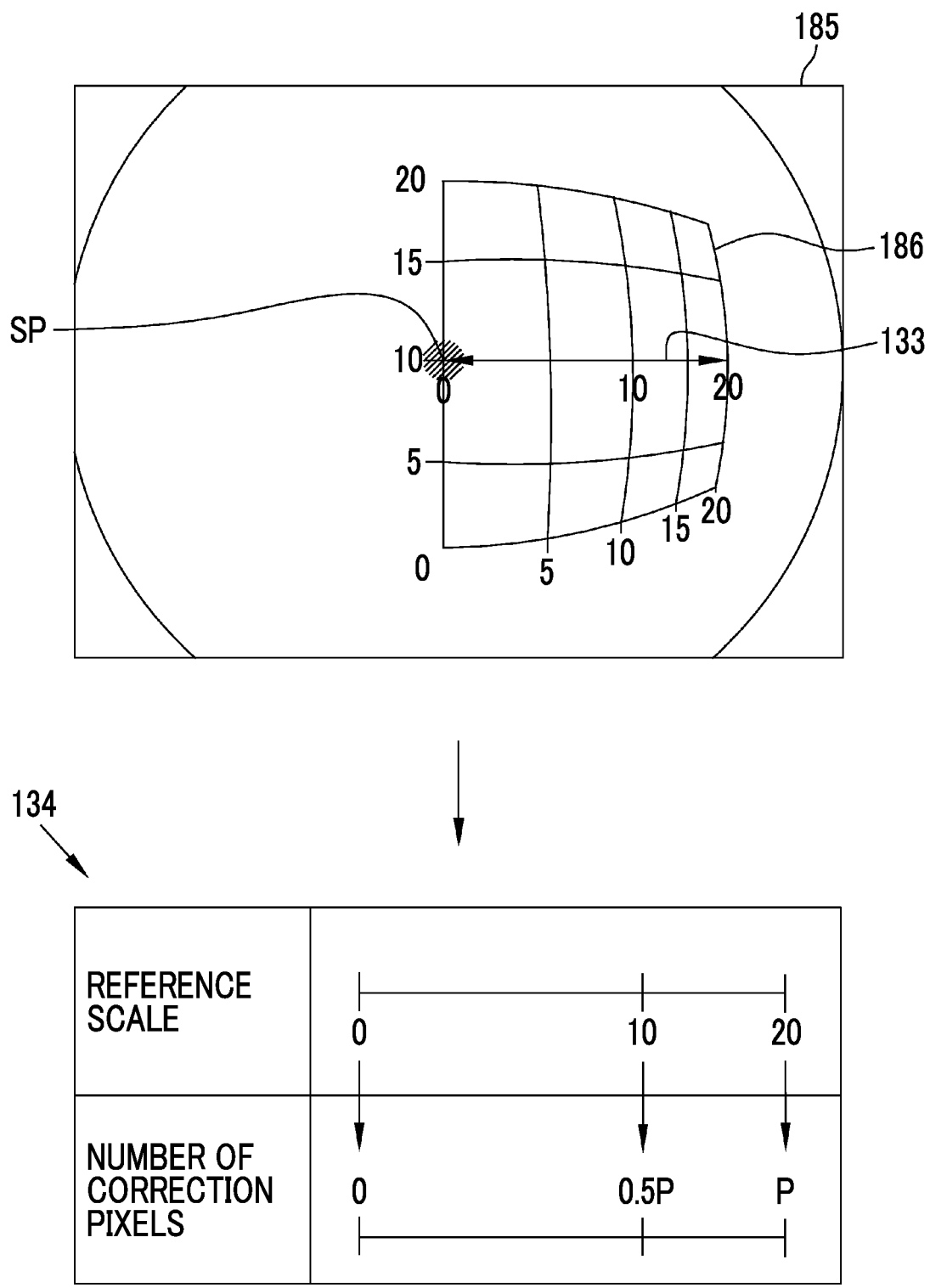
FIG. 27 is an explanatory diagram showing a method of correcting distortion of the reference scale.

In addition, the reference scale setting unit 130 may also use the distortion correction chart image 185 to calculate the reference scale in which the distortion is corrected. In this case, spot-shaped auxiliary measurement light is emitted toward the chart 186, a gridded chart 186 with the same ruled lines (5 mm) as the actual size or finer ruled lines (for example, 1 mm) than the actual size is imaged while changing the observation distance to change the position of the spot SP, and a relationship between the position (pixel coordinates on the imaging surface of the imaging element 46) of the spot and the number of correction pixels (for example, how many pixels the actual size of 5 mm is represented by) corresponding to the actual size is acquired as a correction scale table 134. For example, as shown in FIG. 27, a maximum value "20" of the reference scale 133 is made to correspond to a maximum value P of the correction pixels, and a midpoint "10" of the reference scale 133 is made to correspond to a midpoint 0.5P of the correction pixels.

By virtue of the above configuration, the marker direction candidate position in which the distortion of the lens of the endoscope 12 is taken into consideration can be detected, and the accuracy for determining the display direction of the display marker can be improved.

It is preferable that the specified distance position information is associated with size information indicating the actual size. In this case, the specified distance position information setting unit 180 reads out the setting of "REPRESENTING SPECIFIED DISTANCE POSITION INFORMATION IN ACTUAL SIZE". Next, the candidate distance calculation unit 200 calculates the candidate distance 201 (refer to FIG. 23) from the position of the specific region to the marker direction candidate position as the actual size.

Figure 28:
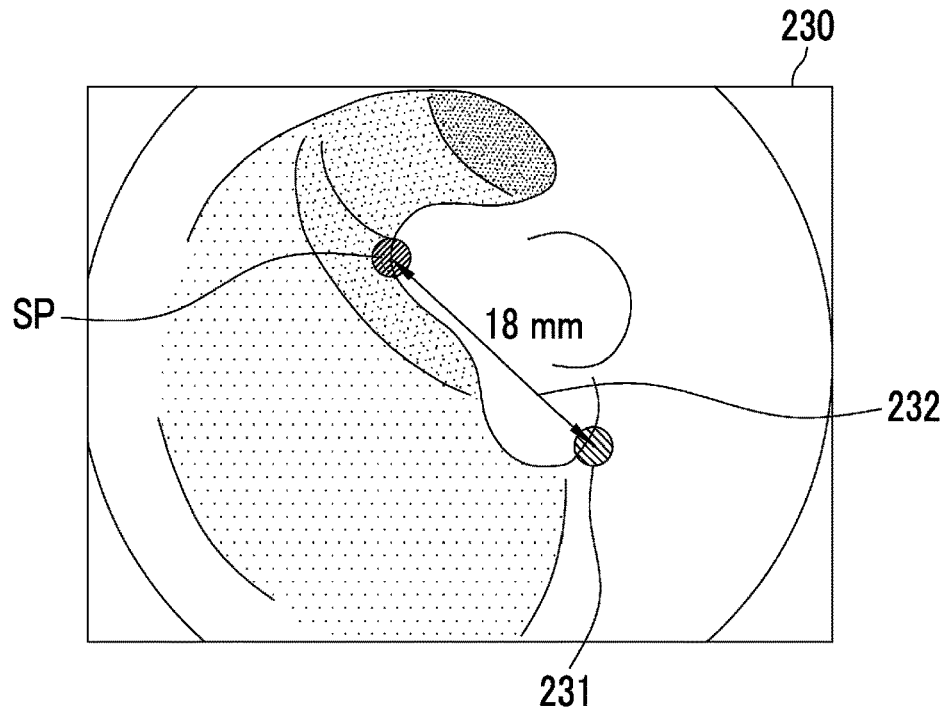
FIG. 28 is an image diagram showing an example of a length measurement image in a case where the display markers are superimposed and displayed at a maximum candidate distance.

In this case, as shown in FIG. 28, the display marker superimposition unit 160 can display the display marker 232 (18 mm in FIG. 28), which is a line segment having the same actual size as the actual size of the region-of-interest, on the length measurement image 230. In addition, in FIG. 28, the display marker 232 is displayed at the maximum candidate distance. The maximum candidate distance superimposed as the display marker 232 is the distance of the actual size from the position of the specific region to the marker direction determination position 231. By virtue of the above configuration, the actual size of the region-of-interest can be directly displayed as the display marker at a time point when the marker direction determination position is determined.

Meanwhile, in a case where the specified distance position information 181 is represented by the number of pixels without associating the specified distance position information with the size information, that is, in a case where the display marker 232 is superimposed and displayed not at the maximum candidate distance in an optional display size such as "20 mm", the calculation processing can be made faster as much as the size information does not correspond to the specified distance position information 181, and the time until the length measurement image on which the display marker is superimposed can be shortened.

In addition, the size information may be associated with the specified distance position information, which is present at a coordinate position closest to the position of the specific region, in the specified distance position information, and the interpolation processing may be performed using the distances of the regular intervals during the calculation of the candidate distance. In a case where the specified distance position information is concentric circles, the innermost circle from the position of the specific region is set as the representative specified distance position information, and the size information is associated with the representative specified distance position information. During the calculation of the candidate distance, the interpolation processing may be performed using the size information associated with the representative concentric circles, the setting information on the distance of the regular intervals, and the information on how many pixels the concentric circles are away from the representative concentric circle the candidate distance, and the candidate distance may be calculated. By virtue of the above configuration, the calculation processing can be made faster as compared to a case where the size information is associated with all the specified distance position information.

Here, as a first modification example, a case where a plurality of marker direction candidate positions are present, which form a candidate distance equal to or larger than the specified distance from the position of the specific region will be described. In this case, it is preferable that the direction determination unit 210 determines the plurality of marker direction determination positions and the display marker superimposition unit 160 generates a length measurement image in which a plurality of display markers having the position of the specific region as the base point and including at least each marker direction determination position are superimposed on the specific region image.

Figure 29:
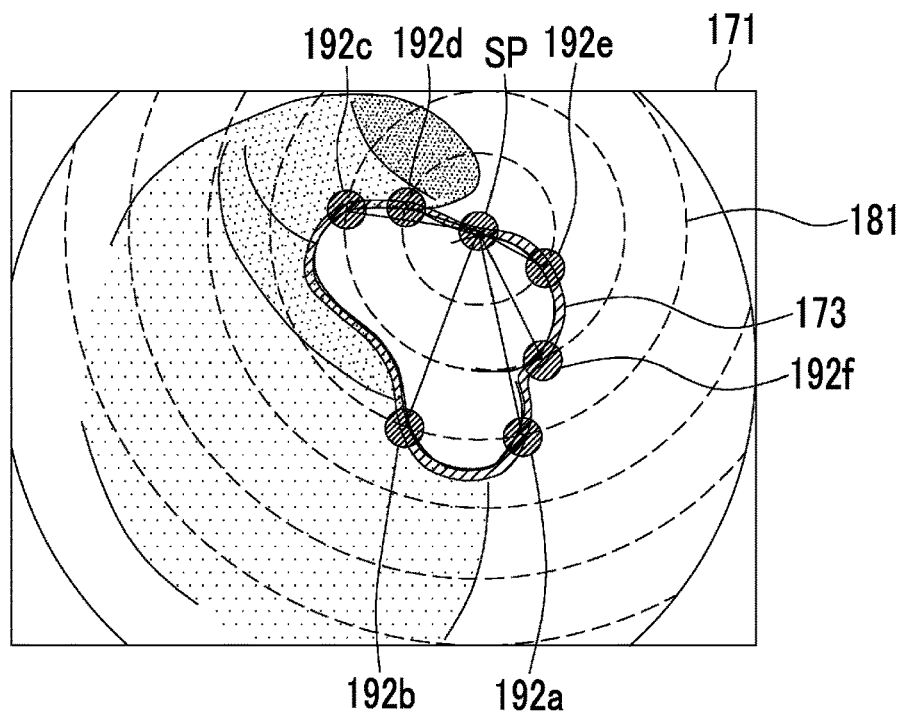
FIG. 29 is an image diagram showing an example in which marker direction candidate positions are shown on an image in a case where a plurality of marker direction determination positions are present.
Figure 30:
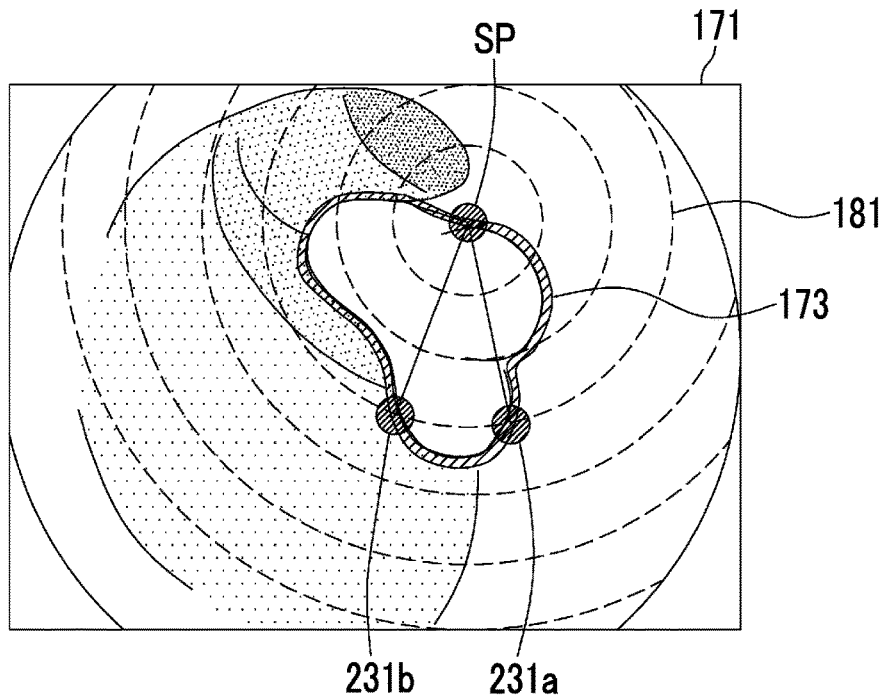
FIG. 30 is an image diagram showing an example in which marker direction determination positions are shown on an image in a case where the plurality of marker direction determination positions are present.

Specific examples will be described. In a specific example of FIG. 29, in a case where the specified distance is set as the maximum candidate distance, two marker direction candidate positions (marker direction candidate positions 192a and 192b) that form the maximum candidate distance with the position of the specific region (spot SP) among the six marker direction candidate positions 192a, 192b, 192c, 192d, 192e, and 192f are present in the specific region image 171. In this case, as shown in FIG. 30, the direction determination unit 210 determines the marker direction candidate position 192a (refer to FIG. 29) as a first marker direction determination position 231a and determines the marker direction candidate position 192b (refer to FIG. 29) as a second marker direction determination positions 231b.

Figure 31:
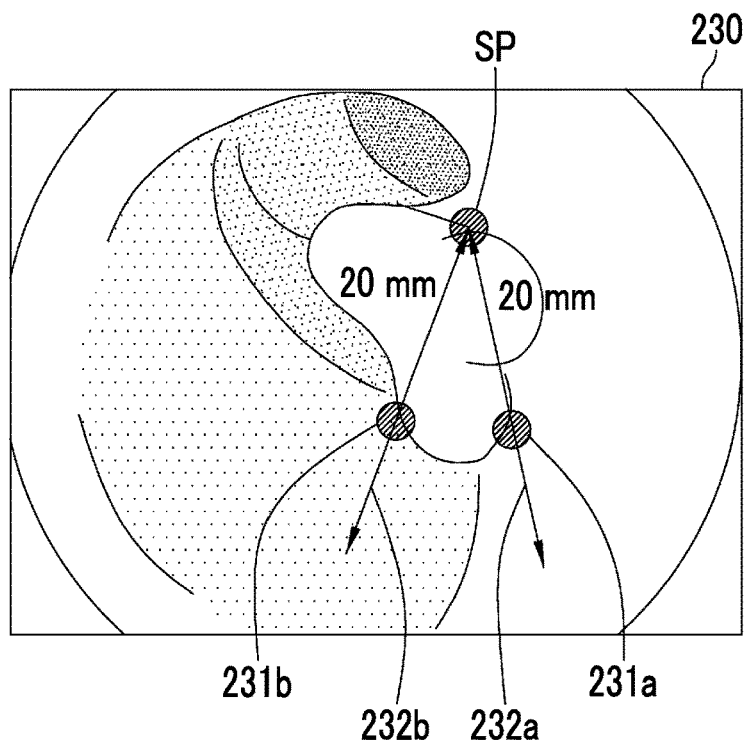
FIG. 31 is an image diagram showing an example of a length measurement image in which a plurality of candidate markers are displayed with each other.

Next, as shown in FIG. 31, the display marker superimposition unit 160 superimposes the plurality of display markers on the specific region image as the candidate markers to generate the length measurement image 230. A first candidate marker 232a passes through the first marker direction determination position 231a. A second candidate marker 232b passes through the second marker direction determination position 231b. By virtue of the above configuration, the plurality of display markers having the same actual size can be displayed. Moreover, it is possible to create an option for selecting a display marker displayed in a direction that is more easily observed by the user.

As shown in FIG. 31, the plurality of candidate markers may be superimposed and displayed on the length measurement image 230 in the same display aspect or may be superimposed and displayed in different display aspects. For example, the first candidate marker 232a may be displayed with a solid line and the second candidate marker 232b may be displayed with a broken line. Additionally, the colors of the first candidate marker 232a and the second candidate marker 232b may be displayed differently from each other. The display aspect of the plurality of candidate markers is not limited to this.

Moreover, it is preferable that the plurality of candidate markers are switched and displayed. Specifically, as shown in FIG. 32, the first length measurement image 230a that displays the first candidate marker 232a and the second length measurement image 230b that displays the second candidate marker 232b are switched and displayed. In FIG. 32, the second candidate marker 232b that is not displayed in the first length measurement image 230a and the first candidate marker 232a that is not displayed in the second length measurement image 230b are shown by a broken line.

In addition, as shown in FIG. 32, display aspects of a candidate marker desired to be most enhanced, and the other candidate markers may be made different from each other for each length measurement image to be switched such that, in the first length measurement image 230a, the first candidate marker 232a is displayed by a solid line, the second candidate marker 232b is displayed by a broken line, and in the second length measurement image 230b, the first candidate marker 232a is shown by a broken line and the second candidate marker 232b is displayed by a solid line. The methods in which the display aspects of the candidate markers are made different from each other may be performed by solid lines or broken lines, or colors or transmittances may be different from each other, and the present invention is not limited to this.

As a switching method, there is a method of providing a candidate marker changeover switch (not shown) on the endoscope 12 or a foot switch or a touch panel serving as the user interface 16 and switching the respective length measurement images 230a and 230b therebetween, using the operation of the candidate marker changeover switch as a trigger. In addition, the switching method is not limited to this. For example, voice recognition, gesture recognition, or visual line recognition (eye tracking) may be used as a trigger for the switching operation.

Additionally, any one candidate marker of the plurality of candidate markers may be determined as the display marker, and only the determined display marker may be displayed on the length measurement image. In this case, a candidate marker selection button may be provided on the endoscope 12 or the user interface 16. Voice recognition, gesture recognition, or visual line recognition may be used as a trigger for the candidate marker selection operation. By virtue of the above configuration, it is possible to select a display marker displayed in the direction that is more easily observed by the user.

Figure 33:
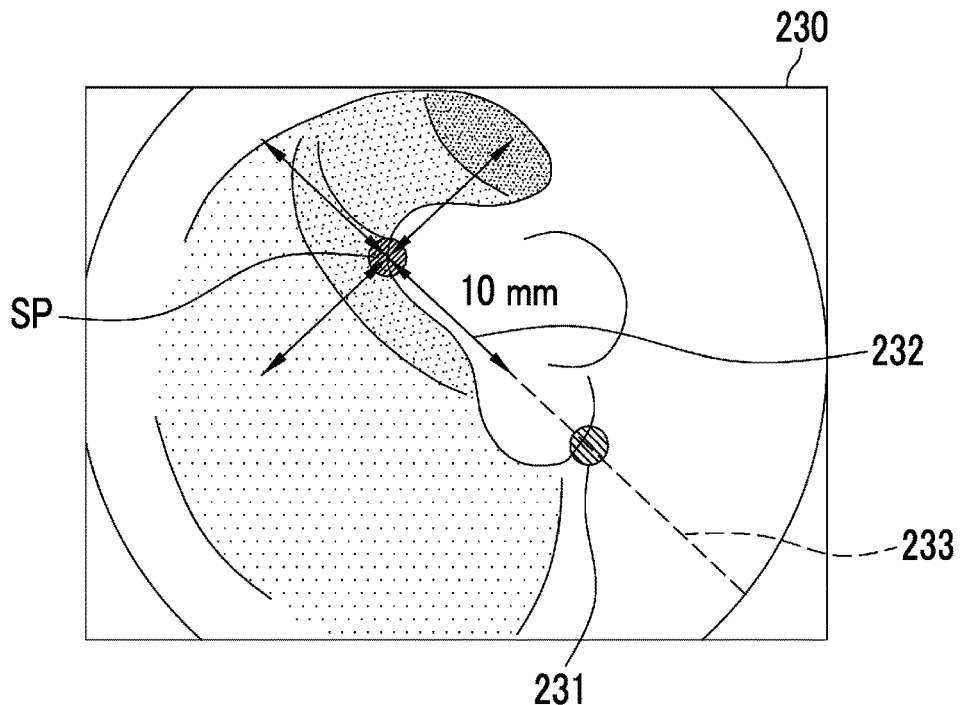
FIG. 33 is an image diagram showing an example of a length measurement image in which a cross-shaped display marker is displayed.

Here, as a second modification example, an example in which the display marker is displayed in a display aspect other than the line segment (arrow) will be described. It is preferable that the display marker superimposition unit 160 displays the display marker 232 on the length measurement image 230 in a marker shape read out by the display marker generation unit 140. For example, as shown in FIG. 33, in a case where the marker shape of the display marker 232 displayed on the length measurement image 230 is a cross shape, an end point of any one of the line segments, which have the base point as the position (spot SP) of the specific region and constitute the cross shape that is the display marker 232, is included on the extension line 233 that has the position (spot SP) of the specific region as the start point and passes through the marker direction determination position 231.

Figure 34:
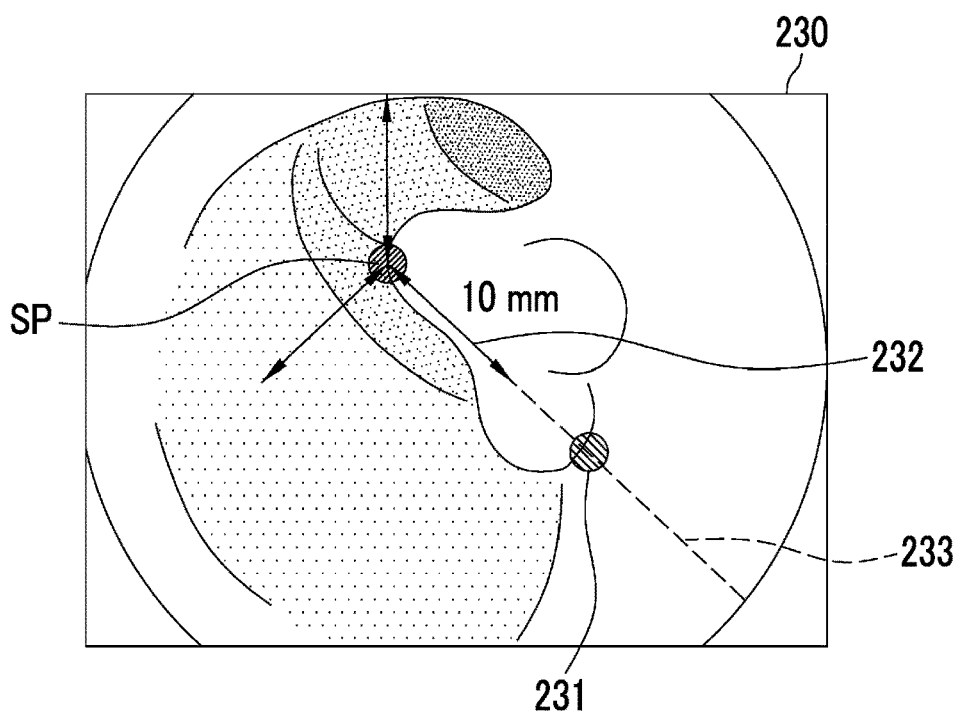
FIG. 34 is an image diagram showing an example of a length measurement image in which a trilinear display marker is displayed.

Additionally, as shown in FIG. 34, in a case where the marker shape of the display marker 232 displayed on the length measurement image 230 is a trilinear shape, an end point of any one of the line segments, which have the base point as the position (spot SP) of the specific region and constitute the trilinear shape, is included on the extension line 233 that has the position (spot SP) of the specific region as the start point and passes through the marker direction determination position 231. In addition, FIGS. 33 and 34 show an example in which the display size of the display marker 232 is set to "DISPLAY AT 10 mm".

Figure 35:
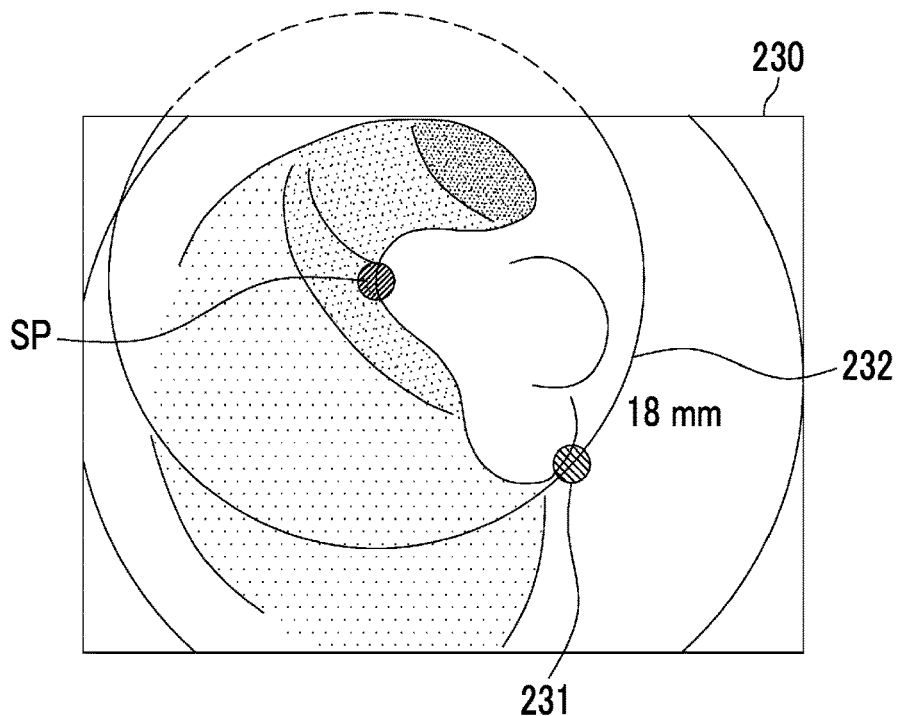
FIG. 35 is an image diagram showing an example of a length measurement image in which a circular display marker is displayed.

Additionally, as shown in FIG. 35, in a case where the marker shape of the display marker 232 displayed on the length measurement image 230 is a circular shape, the center of the display marker 232 is set as the base point. In this case, the base point is set as the position of the specific region (spot SP), and the marker direction determination position 231 is included in a region on or inside a peripheral line of the display marker 232. In the example shown in FIG. 35, the marker direction determination position 231 is included in the peripheral line of the display marker 232. In addition, FIG. 35 shows an example in which the display size of the display marker 232 is set to "DISTANCE AT MAXIMUM CANDIDATE DISTANCE".

Additionally, a portion of the display marker 232 that is displayed on the length measurement image 230 is shown by a solid line, and a portion thereof that is outside the screen and is not displayed on the length measurement image 230 is shown by a broken line.

By showing the display marker in a circular shape, it is possible to visualize whether treatment is to be performed in any range, and it is possible to assist in the selection of the treatment tool. Additionally, by performing a setting such that the display marker is displayed to be larger than the maximum candidate distance, it is possible to visually recognize a range in which a local injection liquid is to be locally injected in a case where the EMR is applied.

Here, a method of extracting the region-of-interest edge information will be described. It is preferable that the region-of-interest edge information extraction unit 170 extracts the region-of-interest edge information from the specific region image by performing the structure enhancement processing on the specific region image. The structure enhancement processing is image processing that performs contrast adjustment processing, edge enhancement processing, and/or binarization processing.

In the contrast adjustment processing, first, a shade histogram in which pixel values (brightness values) are represented on a lateral axis and frequency is represented on a vertical axis is obtained from the acquired specific region image. Next, a distribution function is obtained from the shade histogram. Moreover, in the specific region image, gradation correction is performed such that a portion having a low density is lower and a portion having a high density is higher. In this case, it is preferable to determine a gradation correction operation value to be substituted in the distribution function. Additionally, in a case where the gradation correction is performed, a gradation correction table in which the density and output values are associated with each other may be used.

In the edge enhancement processing, an edge is enhanced by performing, on the pixels constituting the specific region image, image processing in which filters such as an expansion filter, a contraction filter, an averaging filter, and/or a median filter that replaces the density of a center pixel of 3×3 pixels are combined with each other. The expansion filter replaces a pixel having a maximum brightness among the pixels included in the 3×3 pixels with the center pixel. The contraction filter replaces a pixel having a minimum brightness among the pixels included in the 3×3 pixels with the center pixel. The averaging filter sets an average value of pixel values of the pixels included in the 3×3 pixels is set as a pixel value of the center pixel. The median filter sets a median value of the pixels included in the 3×3 pixels as the pixel value of the center pixel.

In the binarization processing, the specific region image is binarized using a binarization processing threshold value. For example, a pixel value possessed by each pixel of the specific region image is referred to, pixels equal to or larger than the binarization processing threshold value are converted in black, and pixels smaller than the binarization processing threshold value are converted in white to obtain a binarized image. The binarization processing may be further performed on the specific region image to which the contrast adjustment processing and/or the edge enhancement processing has been performed. Additionally, the binarization processing may be performed without performing the contrast adjustment processing and/or the edge enhancement processing.

The region-of-interest edge information extraction unit 170 extracts the region-of-interest edge information corresponding to the end part of the region-of-interest reflected in the specific region image as the positional information from the processed specific region image subjected to such structure enhancement processing. By extracting the region-of-interest edge information through the structure enhancement processing, the region-of-interest edge information can be obtained by applying the existing image processing method.

Additionally, it is preferable to extract the region-of-interest edge information by using the region-of-interest edge information extraction unit 170 as a trained model and inputting the specific region image. As models used for generating the trained model, various suitable models can be used for image recognition by machine learning.

It is preferable to adopt deep learning as a model to be used as the trained model by learning. Moreover, it is preferable to adopt a convolutional neural network for the purpose of extracting the region-of-interest edge information from the image. In addition to the deep learning, the machine learning includes decision trees, support vector machines, random forests, regression analysis, supervised learning, semi-supervised learning, unsupervised learning, reinforcement learning, deep reinforcement learning, generative adversarial networks, and the like.

For the learning of the model, it is preferable to use captured images acquired in the past. For example, the region-of-interest edge information generated from the captured images acquired in the past and an original image from which the region-of-interest edge information is extracted are associated with each other to be used as teaching data or test data. Additionally, depending on the type of the model, a captured image that does not have the region-of-interest edge information may be used for learning as a learning image. By extracting the region-of-interest edge information using the trained model, it is possible to improve the accuracy of extracting the region-of-interest edge information.

Figure 36:
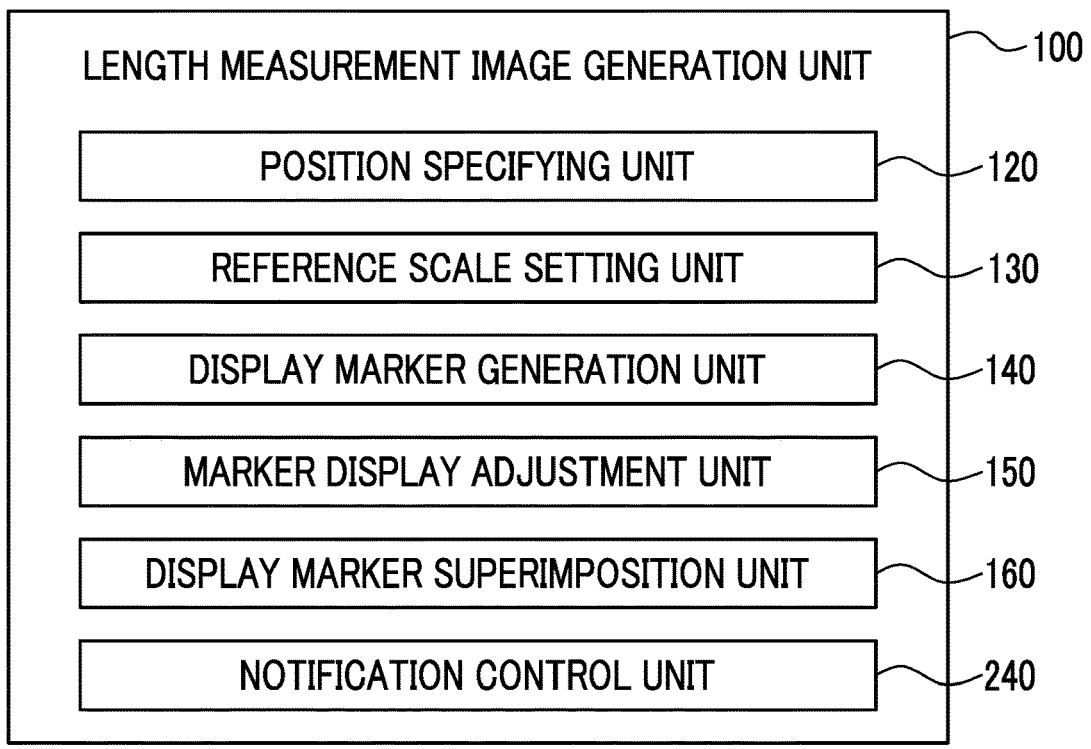
FIG. 36 is a block diagram showing the functions of a length measurement image generation unit provided with a notification control unit.

Here, as a third modification example, an example in which notification for forming a spot at the end part of the region-of-interest is performed will be described. In this case, as shown in FIG. 36, the length measurement image generation unit 100 is further provided with a notification control unit 240. It is preferable that the notification control unit 240 uses the position of the specific region and the region-of-interest edge information to generate a notification instruction for irradiating the end part of the region-of-interest with the spot, and controls to perform notification via the user interface 16.

In a case where the subject includes a three-dimensional region-of-interest, such as a polyp in which a part of the mucous membrane has bulged, and a spot is formed at an apex of the bulge of the region-of-interest (the apex that has bulged toward the distal end part 12d), the size of the display marker displayed on the length measurement image is smaller than that in a case where a spot is formed at a region of origin of the bulge, and there is a concern that the actual size of the entire region-of-interest to be diagnosed or treated may be misunderstood as small. Such a problem occurs because the size of the generated virtual scale differs depending on the position where the spot is formed (refer to FIG. 7). For this reason, by forming a spot on the mucous membrane at a position close to the region of origin of the bulge of the region-of-interest or the region of origin, a display marker for an accurate actual size of the entire region-of-interest can be displayed on the length measurement image.

In order to superimpose and display the display marker indicating the accurate actual size of the entire region-of-interest, it is preferable that the spot formed on the subject with the auxiliary measurement light is formed at the end part of the region-of-interest, that is, at a position indicated by the region-of-interest edge information on the specific region image. Thus, by performing the notification in "a case where the spot is not formed at the end part of the region-of-interest", the user can be prompted to operate the endoscope 12 to form the spot at the end part of the region-of-interest.

First, the notification control unit 240 receives or reads out the information on the position of the specific region specified by the position specifying unit 120 and the region-of-interest edge information from the memory. Next, the region-of-interest edge information and the information on the position of the specific region are referred to, and a notification instruction is transmitted to the system control unit 60 in a case where the coordinate information of both do not overlap each other.

In addition, a distance between the coordinates included in the region-of-interest edge information and the coordinates of the position of the specific region may be calculated, and the notification instruction may be transmitted in a case where the distance is equal to or larger than the notification threshold value. As the notification instruction, there are a notification instruction using a sound such as a buzzer sound or a voice message, and a notification instruction based on visual information such as a notification obtained by providing a notification lamp as the user interface 16 and performing color light emission or blinking of the notification lamp, or a notification for performing message display on the specific region image or the length measurement image. In addition, the notification instruction is not limited to this.

Figure 37:
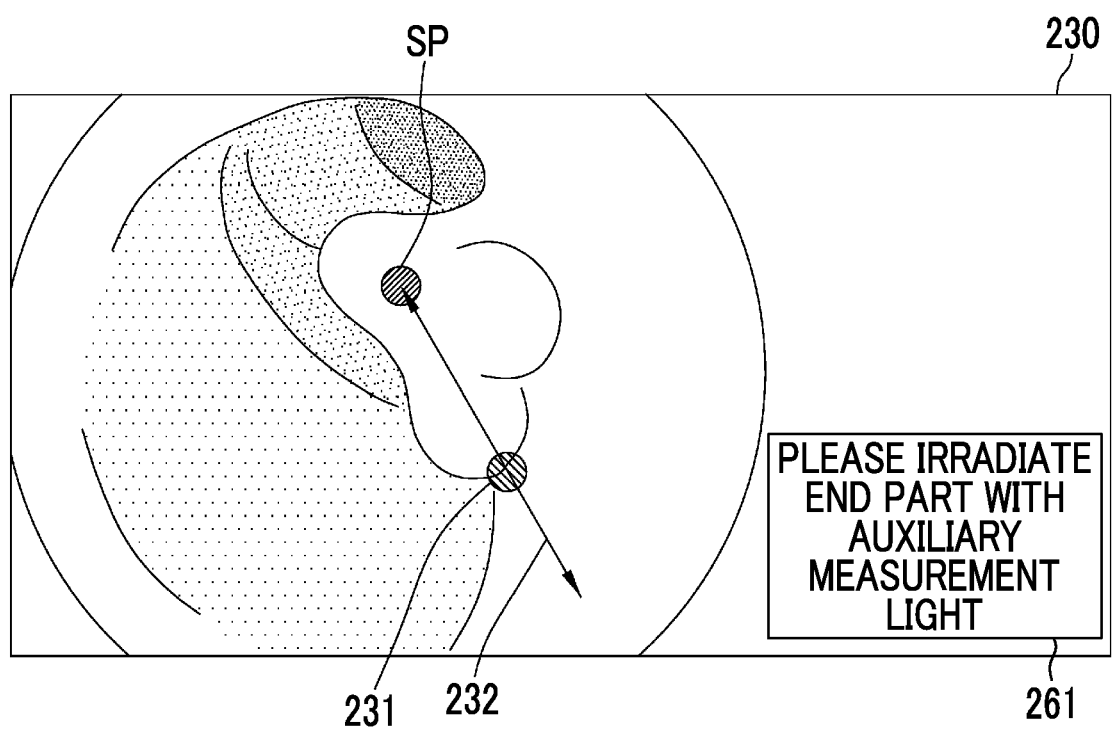
FIG. 37 is an image diagram showing an example of a specific region image in which notification is performed by displaying a message.

A specific example in which notification is performed by the message display of the specific region image will be described with reference to a specific example shown in FIG. 37. The length measurement image 230 includes the spot SP formed on the subject. In a case where the notification control unit 240 determines that the spot SP is "not formed at the end part of the region-of-interest", a message 261 is displayed in a portion of the length measurement image 230 that does not include the subject. In the specific example shown in FIG. 37, the message 261 is displayed as "PLEASE IRRADIATE END PART WITH AUXILIARY MEASUREMENT LIGHT".

In addition, in this case, an instruction regarding the operation of the endoscope 12 may be displayed, such as displaying the message 261 "PLEASE MOVE ENDOSCOPE TO RIGHT BY A CENTIMETER". Additionally, a candidate position of a place where the spot SP is to be formed may be displayed as a candidate spot position on a portion of the specific region image including the subject.

Figure 38:
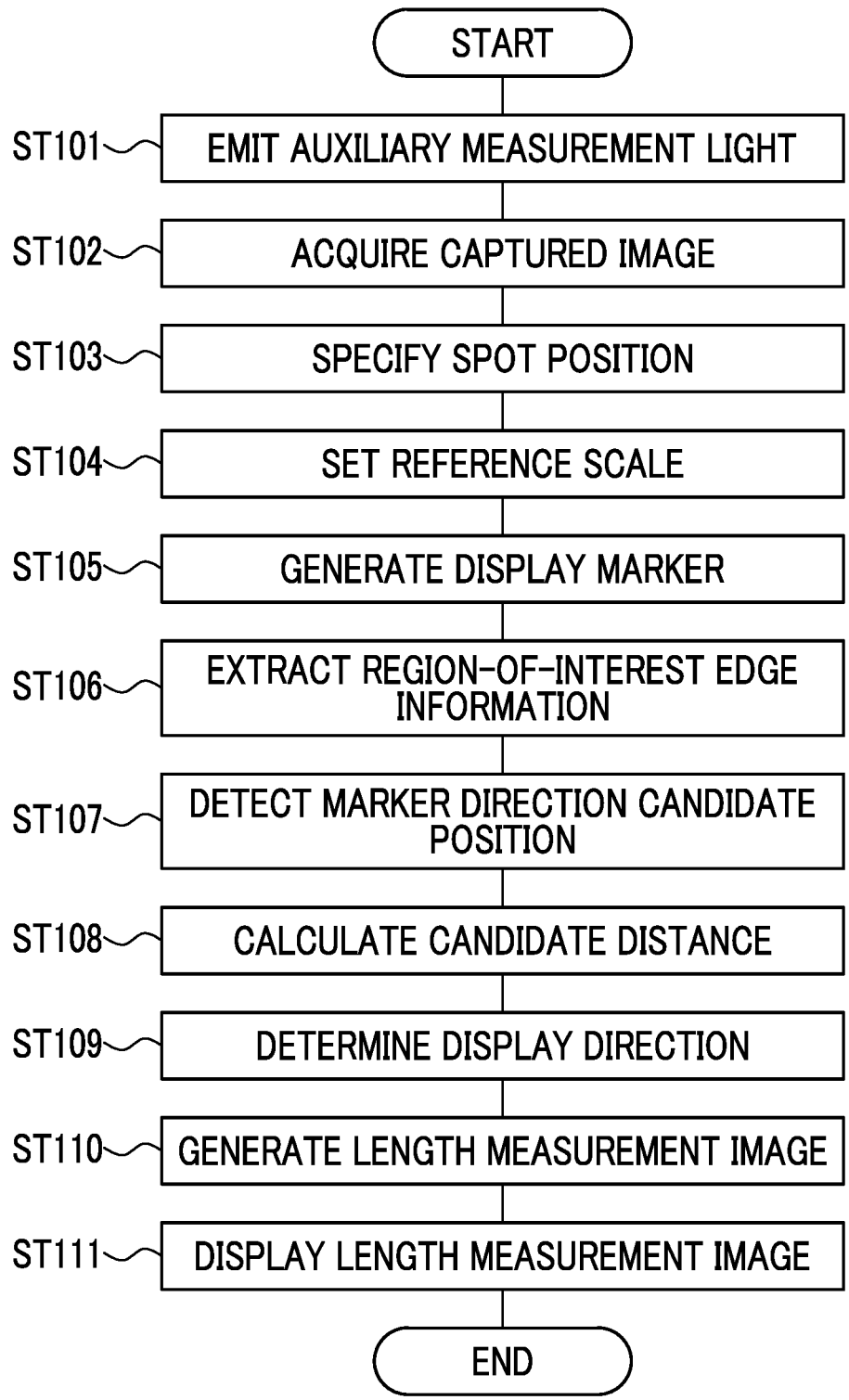
FIG. 38 is a flow chart showing a flow of operation of the endoscope system in a length measurement mode.

A series of flow of the operation of the endoscope system in the length measurement mode of the present embodiment will be described with reference to a flowchart shown in FIG. 38. First, the auxiliary measurement light is emitted (Step ST101), and the subject including a spot formed on the subject with the auxiliary measurement light is imaged to acquire a captured image (specific region image) (Step ST102). Next, the position specifying unit 120 specifies the position of the spot formed on the subject as the position of the specific region of the specific region image (Step ST103). Next, the reference scale setting unit 130 sets a reference scale on the basis of the position of the specific region (Step ST104).

Next, the display marker generation unit 140 generates a display marker to be superimposed and displayed on the specific region image in accordance with the marker shape setting on the basis of the set reference scale (Step ST105). Next, the region-of-interest edge information extraction unit 170 of the marker display adjustment unit 150 extracts region-of-interest edge information (Step ST106). This step may be performed simultaneously with the generation of the reference scale (Step ST104).

Next, the marker direction candidate position detection unit 190 detects at least one or more marker direction candidate positions, using the region-of-interest edge information and the specified distance position information (Step ST107). Next, the candidate distance calculation unit 200 calculates a candidate distance from the position of the specific region to the marker direction candidate position (Step ST108). Next, the direction determination unit 210 determines a marker direction determination position and determines a display direction of the display marker (Step ST109). Next, the display marker superimposition unit 160 superimposes the display marker of which the display direction is determined on the specific region image to generate a length measurement image (Step ST110). Finally, the display control unit 53 displays the length measurement image on the display 15 (Step ST111).

In addition, the length measurement image generation unit 100 may be separated from the processor device 14, and the length measurement image generation unit 100 may be provided in an expanded processor device (not shown). In this case, the expanded processor device may be connected to the processor device 14, the user interface 16, and the display 15.

In the above embodiment, various hardware structures of processing units that execute various types of processing such as the reception unit 51, the signal processing unit 70, the display control unit 53, and the system control unit 60 are various processors as shown below. The various processors include a central processing unit (CPU) that is a general-purpose processor that executes software (programs) to function as various processing units, a programmable logic device (PLD), which is a processor capable of changing the circuit configuration after manufacturing, such as a field programmable gate array (FPGA), a dedicated electric circuit that is a processor having a circuit configuration designed in a dedicated manner to execute various processing, and the like.

One processing unit may be constituted of one of the various processors, or may be constituted of a combination (for example, a plurality of FPGAs or a combination of a CPU and an FPGA) of two or more processors of the same type or different types. Additionally, a plurality of processing units may be constituted of one processor. As an example in which the plurality of processing units is constituted of one processor, firstly, as represented by a computer such as a client or a server, there is a form in which one processor is configured by a combination of one or more CPUs and software and this processor functions as the plurality of processing units. Secondly, as represented by system on chip (SoC), there is a form in which a processor that realizes the functions of the entire system including a plurality of processing units with one integrated circuit ((IC) chip is used. In this way, the various processing units are configured using one or more of the various processors as the hardware structure.

Moreover, the hardware structure of the various processors is, more specifically, an electric circuit (circuitry) in a form in which circuit elements such as semiconductor elements are combined together. Additionally, the hardware structure of the storage unit is a storage device such as a hard disc drive (HDD) or solid state drive (SSD).

EXPLANATION OF REFERENCES

10: endoscope system
12: endoscope
12a: insertion part
12b: operating part
12c: bendable part
12d: distal end part
12e: angle knob
12f: observation mode selector switch
12g: still image acquisition instruction switch 12h: zoom operation part
12j: forceps port
13: light source device
14: processor device
15: display
16: user interface
20: light source unit
21: light source control unit
22: light guide
31: objective lens
32: illumination lens
33: auxiliary measurement light lens
34: opening
35: air and water supply nozzle
44a: illumination optical system
44b: imaging optical system
45: auxiliary measurement light emission unit
45a: light source for auxiliary measurement light
45b: auxiliary measurement light generation element
45c: prism
46: imaging element
47: imaging control unit
48: CDS/AGC circuit
49: analog/digital (A/D) converter
50: communication I/F
51: reception unit
52: image saving unit
53: display control unit
60: system control unit
70: signal processing unit
80: normal light image generation unit
90: special light image generation unit
100: length measurement image generation unit
120: position specifying unit
121, 171: specific region image
122: region-of-interest
130: reference scale setting unit
131: scale table
132, 230: length measurement image
133: reference scale
134: correction scale table
140: display marker generation unit
141: marker shape setting unit
142: marker shape setting image
143: radio button
150: marker display adjustment unit
160: display marker superimposition unit
170: region-of-interest edge information extraction unit
173: region-of-interest edge information
180: specified distance position information setting unit
181: specified distance position information
185: distortion correction chart image
186: chart
190: marker direction candidate position detection unit
191, 191a, 191b, 191c, 191d, 191e, 191f, 191g, 192a, 192b, 192c, 192d, 192e, 192f: marker direction candidate position
200: candidate distance calculation unit
201: candidate distance
210: direction determination unit
220: display size setting unit
221: display size setting image
222: display size input field
231: marker direction determination position
231a: first marker direction determination position
231b: second marker direction determination position
232: display marker
232a: first candidate marker
232b: second candidate marker
233: extension line
234: marker size display field
240: notification control unit
261: message

What is claimed is:

1. An endoscope system comprising:
an imaging element that images a subject;
a light source for auxiliary measurement light that emits auxiliary measurement light used for measuring the subject; and
a processor configured to:
acquire a captured image obtained by imaging the subject including a specific region formed by the auxiliary measurement light;
specify a position of the specific region in the captured image;
set a reference scale indicating an actual size of the subject on the basis of the position of the specific region;
generate a display marker to be superimposed on the captured image on the basis of the reference scale;
extract region-of-interest edge information from the captured image;
detect, as a marker direction candidate position used for determining a display direction of the display marker, an intersection point where the region-of-interest edge information and specified distance position information overlap each other, the specified distance position information indicating a position separated from the position of the specific region by a certain specified interval from the position of the specific region, wherein the region-of-interest edge information and the specified distance position information are coordinate information processed inside the processor;
calculate a candidate distance, which is a distance from the position of the specific region to the marker direction candidate position, from the specified distance position information;
determine the marker direction candidate position, which forms the candidate distance equal to or larger than a specified distance from the position of the specific region, as a marker direction determination position;
create a length measurement image in which the display marker that has the position of the specific region as a start point and passes through a part of an extension line passing through the marker direction determination position is superimposed on the captured image such that the position of the specific region is used as a base point; and
display the length measurement image.

2. The endoscope system according to claim 1, wherein the specified distance position information is information indicating equal interval positions from the position of the specific region.

3. The endoscope system according to claim 1, wherein the specified distance position information is concentric circles centered on the position of the specific region.

4. The endoscope system according to claim 1, wherein distortion of the specified distance position information is corrected.

5. The endoscope system according to claim 1,
wherein the specified distance position information is associated with size information indicating the actual size.

6. The endoscope system according to claim 5,
wherein the processor is configured to set the specified distance position information, which is closest to the position of the specific region, in the specified distance position information as representative specified distance position information and associate the size information with the representative specified distance position information.

7. The endoscope system according to claim 5,
wherein the display marker is a line segment having the position of the specific region as a base point and having the marker direction determination position as an end point, and
the processor is configured to display a length of the actual size of the display marker, which is a distance from the position of the specific region to the marker direction determination position, on the basis of the size information.

8. The endoscope system according to claim 1,
wherein the processor is configured to display a plurality of candidate markers as the display markers on the length measurement image in a case where a plurality of the marker direction determination positions are present.

9. The endoscope system according to claim 8,
wherein the processor is configured to switch and display the plurality of candidate markers in the length measurement image.

10. The endoscope system according to claim 1,
wherein the display marker consists of a plurality of line segments having the position of the specific region as a base point, and
one of the plurality of line segments has the position of the specific region as a start point and includes an end point on the extension line that passes through the marker direction determination position.

11. The endoscope system according to claim 1,
wherein the region-of-interest edge information is extracted by structure enhancement processing.

12. The endoscope system according to claim 1,
wherein the region-of-interest edge information is extracted using a trained model.

13. The endoscope system according to claim 12,
wherein the trained model is a convolutional neural network.

14. The endoscope system according to claim 1,
wherein the processor is configured to generate a notification instruction by using the position of the specific region and the region-of-interest edge information to irradiate an end part of a region-of-interest with the auxiliary measurement light.

15. An endoscope system operation method comprising:
a step of imaging a subject;
a step of emitting auxiliary measurement light used for measuring the subject;
a step of acquiring a captured image obtained by imaging the subject including a specific region formed by the auxiliary measurement light;
a step of specifying a position of the specific region in the captured image;
a step of setting a reference scale indicating an actual size of the subject on the basis of the position of the specific region;
a step of generating a display marker to be superimposed on the captured image on the basis of the reference scale;
a step of extracting region-of-interest edge information from the captured image;
a step of detecting, as a marker direction candidate position used for determining a display direction of the display marker, an intersection point where the region-of-interest edge information and specified distance position information overlap each other, the specified distance position information indicating a position separated from the position of the specific region by a certain specified interval from the position of the specific region, wherein the region-of-interest edge information and the specified distance position information are coordinate information processed inside a processor;
a step of calculating a candidate distance, which is a distance from the position of the specific region to the marker direction candidate position, from the specified distance position information;
a step of determining the marker direction candidate position, which forms the candidate distance equal to or larger than a specified distance from the position of the specific region, as a marker direction determination position;
a step of creating a length measurement image in which the display marker that has the position of the specific region as a start point and passes through a part of an extension line passing through the marker direction determination position is superimposed on the captured image such that the position of the specific region is used as a base point; and
a step of displaying the length measurement image.

* * * * *